(12) United States Patent
Hong et al.

(10) Patent No.: US 10,121,064 B2
(45) Date of Patent: Nov. 6, 2018

(54) SYSTEMS AND METHODS FOR BEHAVIOR DETECTION USING 3D TRACKING AND MACHINE LEARNING

(71) Applicant: California Institute of Technology, Pasadena, CA (US)

(72) Inventors: Weizhe Hong, Pasadena, CA (US); David J. Anderson, Altadena, CA (US); Pietro Perona, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 105 days.

(21) Appl. No.: 15/183,747

(22) Filed: Jun. 15, 2016

(65) Prior Publication Data
US 2017/0046567 A1 Feb. 16, 2017
US 2017/0161554 A9 Jun. 8, 2017

Related U.S. Application Data

(60) Provisional application No. 62/148,663, filed on Apr. 16, 2015, provisional application No. 62/205,556, filed on Aug. 14, 2015.

(51) Int. Cl.
*G06K 9/00* (2006.01)
*G06T 7/00* (2017.01)
(Continued)

(52) U.S. Cl.
CPC ............ *G06K 9/00335* (2013.01); *A61B 5/11* (2013.01); *A61B 5/16* (2013.01); *A61B 5/40* (2013.01);
(Continued)

(58) Field of Classification Search
None
See application file for complete search history.

(56) References Cited

U.S. PATENT DOCUMENTS

2003/0028327 A1* 2/2003 Brunner ................ A01K 1/031
                                                                    702/19
2004/0131254 A1    7/2004 Liang et al.
(Continued)

FOREIGN PATENT DOCUMENTS

WO    2013170129 A1    11/2013
WO    2016168869       10/2016

OTHER PUBLICATIONS

Kim et al., ("Multi-Object Detection and Behavior Recognition from Motion 3D Data", IEEE, 2011, pp. 37-42, Published in: Computer Vision and Pattern Recognition Workshops (CVPRW), 2011 IEEE Computer Society Conference on: Date of Conference: Jun. 20-25, 2011).*

(Continued)

*Primary Examiner* — Weiwen Yang
(74) *Attorney, Agent, or Firm* — KPPB LLP

(57) ABSTRACT

Systems and methods for performing behavioral detection using three-dimensional tracking and machine learning in accordance with various embodiments of the invention are disclosed. One embodiment of the invention involves a the classification application that directs a microprocessor to: identify at least a primary subject interacting with a secondary subject within a sequence of frames of image data including depth information; determine poses of the subjects; extract a set of parameters describing the poses and movement of at least the primary and secondary subjects; and detect a social behavior performed by at least the primary subject and involving at least the second subject using a classifier trained to discriminate between a plurality (Continued)

of social behaviors based upon the set of parameters describing poses and movement.

42 Claims, 22 Drawing Sheets

(51) Int. Cl.
    G06K 9/62    (2006.01)
    G06T 7/174    (2017.01)
    A61B 5/11    (2006.01)
    A61B 5/00    (2006.01)
    A61B 5/16    (2006.01)
    H04N 13/25    (2018.01)
    H04N 13/00    (2018.01)
(52) U.S. Cl.
    CPC ............ *A61B 5/4848* (2013.01); *G06K 9/627* (2013.01); *G06K 9/6269* (2013.01); *G06T 7/0004* (2013.01); *G06T 7/174* (2017.01); *H04N 13/25* (2018.05); *G06T 2207/10016* (2013.01); *G06T 2207/10024* (2013.01); *G06T 2207/10028* (2013.01); *H04N 2013/0081* (2013.01)

(56) References Cited

U.S. PATENT DOCUMENTS

| 2004/0141636 | A1* | 7/2004 | Liang .................... A61B 5/1113 382/110 |
| 2010/0111359 | A1 | 5/2010 | Bai et al. |
| 2011/0007946 | A1 | 1/2011 | Liang et al. |
| 2014/0204013 | A1 | 7/2014 | O'prey et al. |
| 2015/0223731 | A1* | 8/2015 | Sahin ........................ A61B 5/16 600/301 |
| 2015/0282766 | A1* | 10/2015 | Cole .................... A61B 5/7267 702/139 |
| 2016/0191335 | A1 | 6/2016 | Effros et al. |

OTHER PUBLICATIONS

International Preliminary Report on Patentability for International Application PCT/US2016/037713, Report issued Oct. 17, 2017, dated Oct. 26, 2017 13 Pgs.
International Search Report and Written Opinion for International Application No. PCT/US2016/037713, Search completed Sep. 21, 2016, dated Sep. 22, 2016, 16 Pgs.
"Movie S2", Retrieved from: http://movie-usa.glencoesoftware.com/video/10.1073/pnas.1515982112/video-2, 1 pg.; linked from Hong et al., "Automated measurement of mouse social behaviors using depth sensing, video tracking, and machine learning", PNAS, 112(38) E5351-E5360, Sep. 22, 2015, published ahead of print: Sep. 9, 2015, Retrieved from: http://www.pnas.org/content/112/38/E5351.
"Movie S3", Retrieved from: http://movie-usa.glencoesoftware.com/video/10.1073/pnas.1515982112/video-3, 1 pg.; linked from Hong et al., "Automated measurement of mouse social behaviors using depth sensing, video tracking, and machine learning", PNAS, 112(38) E5351-E5360, Sep. 22, 2015, published ahead of print: Sep. 9, 2015, Retrieved from: http://www.pnas.org/content/112/38/E5351.
"Movie S4", Retrieved from: http://movie-usa.glencoesoftware.com/video/10.1073/pnas.1515982112/video-4, 1 pg.; linked from Hong et al., "Automated measurement of mouse social behaviors using depth sensing, video tracking, and machine learning", PNAS, 112(38) E5351-E5360, Sep. 22, 2015, published ahead of print: Sep. 9, 2015, Retrieved from: http://www.pnas.org/content/112/38/E5351.
Anderson et al., "Toward a Science of Computational Ethology", Neuron 84, 18-31, doi:10.1020/j.neuron.2014.09.005 (2014).
Bolivar et al., "Assessing Autism-like Behavior in Mice: Variations in Social Interactions Among Inbred Strains", Behav Brain Res. 176(1): 21-26 (2007).
Branson et al., "High-throughput ethomics in large groups of Drosophila", Nature Methods 6, 451-457, doi:10.1038/nmeth.1328 (May 3, 2009).
Burgos-Artizzu et al., "Robust face landmark estimation under occlusion", Computer Vision (ICCV), 2013 IEEE International Conference, 1513-1520 (2013).
Burgos-Artizzu et al., "Social behavior recognition in continuous video", Computer Vision and Pattern Recognition (CVPR), 2012 IEEE Conference, 1322-1329 (2012).
Button et al., "Power failure: why small sample size undermines the reliability of neuroscience", Nature Reviews Neuroscience 14(5): 365-376 (2013).
Cai et al., "Central amygdala PKC-δ+ neurons mediate the influence of multiple anorexigenic signals", Nature Neuroscience 17(9): 1240-1248 (2014).
Camgoz et al., "Gesture Recognition using Template Based Random Forest Classifiers", Computer Vision, ECCV 2014 Workshops, 2014, 16 pgs.
Card et al., "Performance trade-offs in the flight initiation of *Drosophila*", The Journal of Experimental Biology 211(Pt 3): 341-353 (2008).
Chen et al., "Imaging Neuronal Populations in Behaving Rodents: Paradigms for Studying Neural Circuits Underlying Behavior in the Mammalian Cortex", The Journal of Neuroscience: the official journal of the Society for Neuroscience 33(45): 17631-17640 (2013).
Dankert et al., "Automated Monitoring and Analysis of Social Behavior in Ddrosophila", Nat. Methods, Apr. 2009, vol. 6, No. 4, 17 pgs.
De Chaumont et al., "Computerized video analysis of social interactions in mice", Nature Methods 9, 410-417, doi:10.1038/nmeth.1924 (2012).
Deisseroth et al., "Engineering Approaches to Illuminating Brain Structure and Dynamics", Neuron 80(3): 568-577 (2013).
Desland et al., "Manual versus Automated Rodent Behavioral Assessment: Comparing Efficacy and Ease of Bederson and Garcia Neurological Deficit Scores to an Open Field Video-Tracking System", Journal of Central Nervous System Disease 6: 7-14 (2014).
Dollar et al., "Cascaded Pose Regression", CVPR, 2010, pp. 1078-1085.
Ellegood et al., "Behavioral and Neuroanatomical Phenotypes in Mouse Models of Autism", Neurotherapeutics: The journal of the American Society for Experimental NeuroTherapeutics 12(3): 521-533 (2015).
Eyjolfsdottir et al., "Detecting social actions of fruit flies", Computer Vision-ECCV (2014).
Fontaine et al., "Wing and body motion during flight initiation in *Drosophila* revealed by automated visual tracking", The Journal of Experimental Biology 212(Pt 9): 1307-1323 (2009).
Gomez-Marin et al., "Automated Tracking of Animal Posture and Movement during Exploration and Sensory Orientation Behaviors", PLoS ONE 7(8):e41642 (2012).
Gomez-Marin et al., "Big behavioral data: psychology, ethology and the foundations of neuroscience", Nature Neuroscience 17, 1455-1462, doi:10.1038/nn.3812 (2014).
Gonalves et al., "Preliminary Study on determining stereotypical motor movements", Conference Proceedings: . . . Annual International Conference of the IEEE Engineering in Medicine and Biology Society. IEEE Engineering in Medicine and Biology Society Conference 2012, 1598-1601, doi:10.1109/EMBC.2012.6346250 (2012).
Guillot et al., "Intermale aggression and dark/light preference in ten inbred mouse strains", Behavioral Brain Research, 77(1-2), May 1996.
Hong et al., "Automated measurement of mouse social behaviors using depth sensing, video tracking, and machine learning", PNAS, 112(38) E5351-E5360, Sep. 22, 2015, published ahead of print: Sep. 9, 2015, Retrieved from: http://www.pnas.org/content/112/38/E5351.

(56) References Cited

OTHER PUBLICATIONS

Hong et al., "Automated measurement of mouse social behaviors using depth sensing, video tracking, and machine learning", PNAS, 112(38) E5351-E5360, Sep. 22, 2015, published ahead of print: Sep. 9, 2015, Retrieved from: http://www.pnas.org/content/pnas/112/38/E5351.full.pdf.

Iddan et al., "3D Imaging in the Studio (and Elsewhere . . . )", Photonics West 2001—Electronic Imaging eds. Corner, B.D., Nurre, J. H., and Pargas, R. P. (SPIE), 48-55 (2001).

Iyengar et al., "Automated quantification of locomotion, social interaction, and mate preference in *Drosophila mutants*", Journal of Neurogenetics 26(3-4): 306-316 (2012).

Kabra et al., "JAABA: interactive machine learning for automatic annotation of animal behavior", Nature Methods, vol. 10, No. 1, doi:10.1038/nmeth.2281, pp. 64-67, Jan. 2013, published online Dec. 2, 2012.

Knoop et al., "Sensor Fusion for 3D Human Body Tracking with an Articulated 3D Body Model", Proceedings 2006 IEEE International Conference on Robotics and Automation, ICRA 2006, May 15-19, 2006, Orlando, FL.

Kohlhoff et al., "The iFly tracking system for an automated locomotor and behavioural analysis of *Drosophila melanogaster*", Integrative Biology: quantitative biosciences from nano to macro 3(7): 755-760 (2011).

Kulikov et al., "Application of 3-D imaging sensor for tracking minipigs in the open field test", Journal of neuroscience methods 235, 2014, pp. 219-225.

Lin et al., "Functional identification of an aggression locus in the mouse hypothalamus", Nature 470(7333): 221-226 (2011).

Luo et al., "Genetic Dissection of Neural Circuits", Neuron 57, 634-660, doi:10.1016/j.neuron.2008.01.002 (2008).

Lyons et al., "A Kinect-based system for automatic recording of some pigeon behaviors", Behavior Research Methods, doi:10.3758/s13428-014-0531-6 (2014).

Matsumoto et al., "A 3D-Video-Based Computerized Analysis of Social and Sexual Interactions in Rats", PLoS ONE 8, e78460, doi:10.1371/journal.pone.0078460 (2013).

McFarlane et al., "Autism-like behavioral phenotypes in BTBR T1tf/J mice", Genes, Brain and Behavior 7(2): 152-163 (2008).

Miranda et al., "Real-time gesture recognition from depth data through key poses learning and decision forests", 2012 25th SIBGRAPI Conference on Graphics, Patterns and Images, Aug. 22-25, 2012, Ouro Preto, Brazil, 9 pgs.

Mirat et al., "ZebraZoom: an automated program for high-throughput behavioral analysis and categorization", Frontiers in Neural Circuits, vol. 7, Article 107, Jun. 12, 2013, 12 pgs.

Nestler et al., "Animal models of neuropsychiatric disorders", Nature Neuroscience 13(10): 1161-1169 (2010).

Noldus et al., "EthoVision: A versatile video tracking system for automation of behavioral experiments", Behavior Research Methods, Instruments, & Computers: a journal of the Psychonomic Society, Inc. 33(3): 398-414 (2001).

Ohayon et al., "Automated multi-day tracking of marked mice for the analysis of social behavior", Journal of Neuroscience Methods 219, 10-19, doi:10.1016/j.jneumeth.2013.05.013 (2013).

Ou-Yang et al., "An infrared range camera-based approach for three-dimensional locomotion tracking and pose reconstruction in a rodent", Journal of Neuroscience Methods 201(1): 116-123 (2011).

Perez-Escudero et al., "idTracker: tracking individuals in a group by automatic identification of unmarked animals", Nature Methods, vol. 11, No. 7, Jul. 2014, 44 pgs.

Pham et al., "Automated scoring of fear related behavior using EthoVision software", Journal of Neuroscience Methods 178(2): 323-326 (2009).

Post et al., "Gene—environment interaction influences anxiety-like behavior in ethologically based mouse models", Behavioural Brain Research 218(1): 99-105 (2011).

Shemesh et al., "High-order social interactions in groups of mice", eLife 2:e00759 (2013).

Silverman et al., "Behavioural phenotyping assays for mouse models of autism", Nature Reviews Neuroscience 11, 490-502, doi:10.1038/nrn2851 (2010).

Spink et al., "The EthoVision video tracking system—A tool for behavioral phenotyping of transgenic mice", Physiology & Behavior 73(5): 731-744 (2001).

Tsai et al., "Image Tracking Study on Courtship Behavior of Drosophila", PLoS One 7(4):e34784 (2012).

Tzschentke, "Measuring reward with the conditioned place preference (CPP) paradigm: update of the last decade", Addiction Biology, 12(3-4), Sep. 2007, pp. 227-462.

Walf et al., "The use of the elevated plus maze as an assay of anxiety-related behavior in rodents", Nature Protocols 2(2): 322-328 (2007).

Wang et al., "Mining Actionlet Ensemble for Action Recognition with Depth Cameras", 2012 IEEE Conference on Computer Vision and Pattern Recognition, Jun. 16-21, 2012, Providence, RI, 8 pgs.

Weissbrod et al., "Automated long-term tracking and social behavioural phenotyping of animal colonies within a semi-natural environment", Nature Communications 4:2018 (2013).

Wolf et al., "High-Resolution Analysis of Ethanol-Induced Locomotor Stimulation in *Drosophila*", The Journal of Neuroscience: the official journal of the Society for Neuroscience 22(24): 11035-11044 (2002).

Yang et al., "Articulated pose estimation with flexible mixture-of-parts", Computer Vision and Pattern Recognition (CVPR), 2011 IEEE Conference on, Providence, RI, 2011, pp. 1385-1392.

Zhang et al., "Circuit-breakers: optical technologies for probing neural signals and systems", Nature Reviews: Neuroscience 8(8): 577-581 (2007).

\* cited by examiner

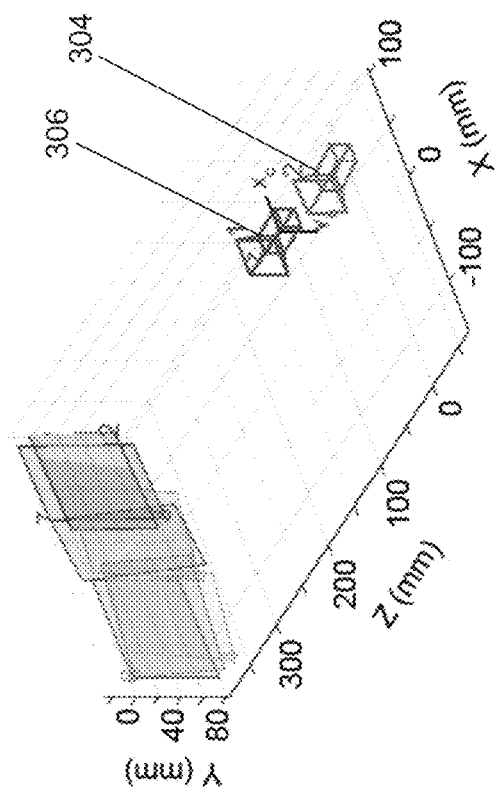
FIG. 3C
FIG. 3D
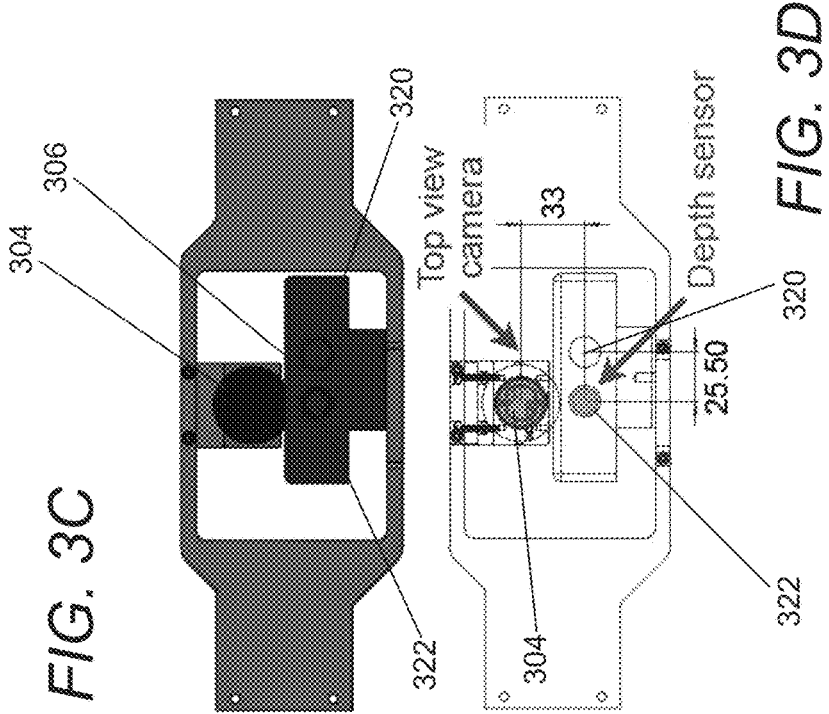
FIG. 6E

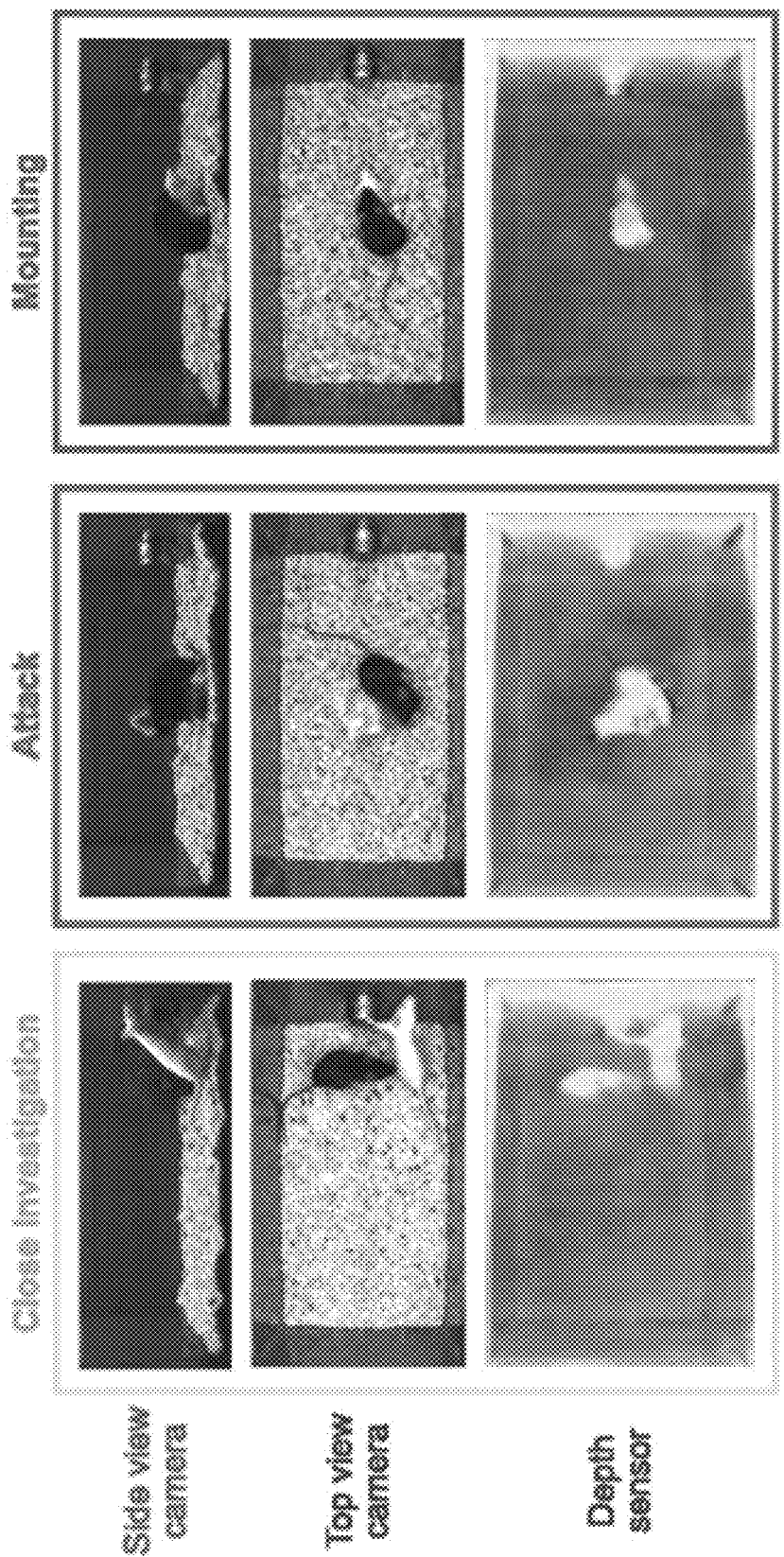

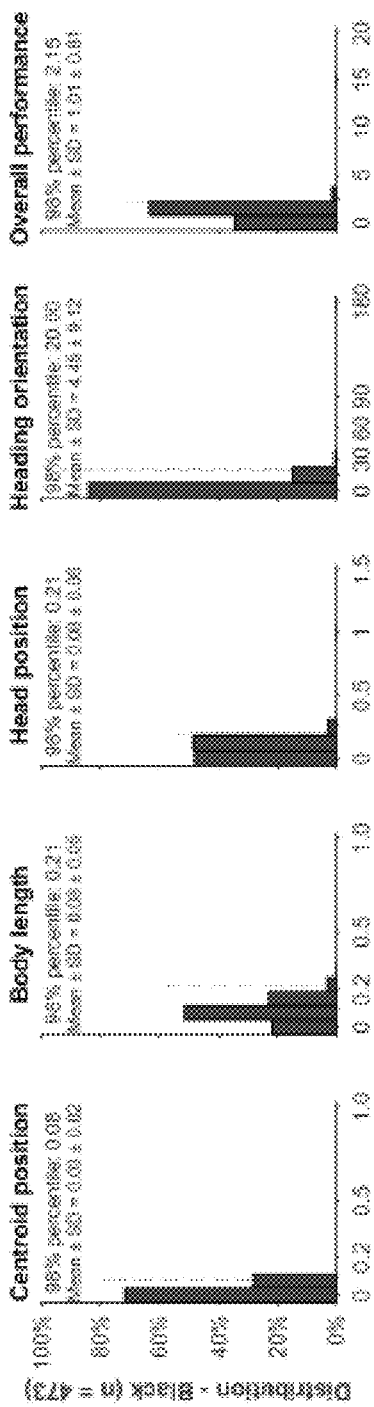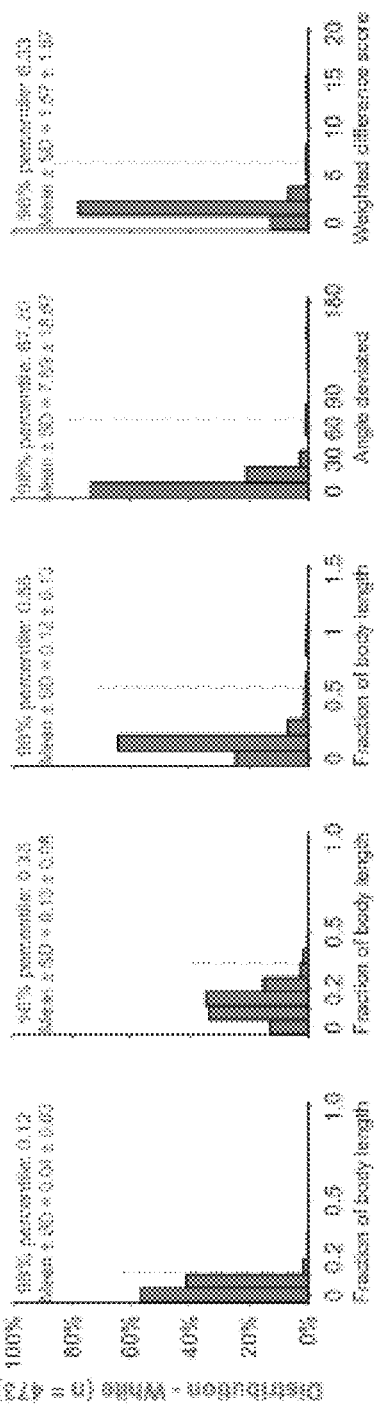

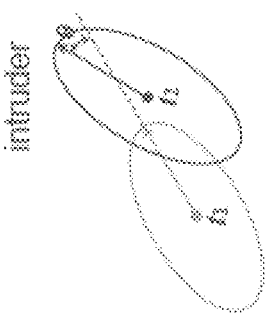
FIG. 12A
FIG. 12B
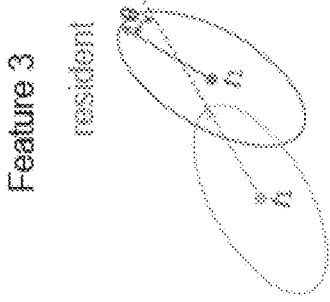
FIG. 12C
FIG. 12D
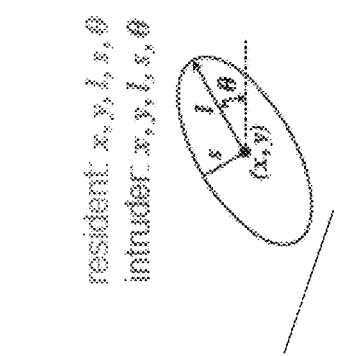
FIG. 12E
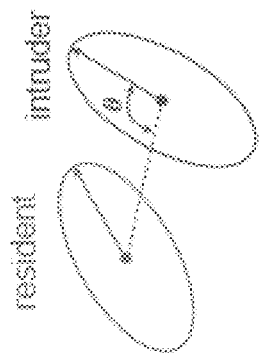
FIG. 12F
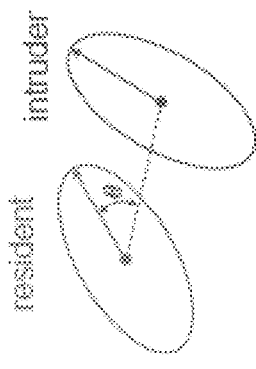

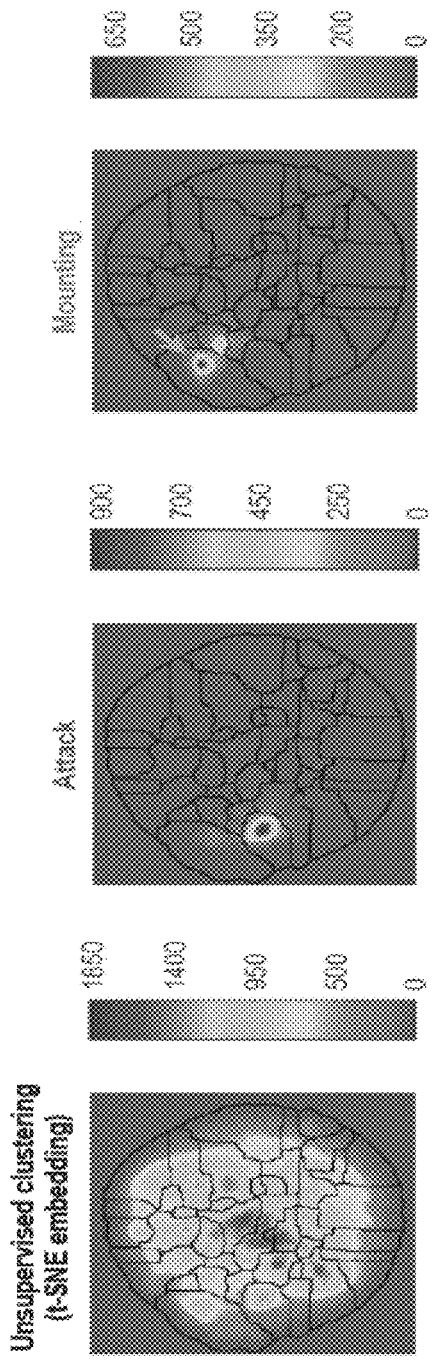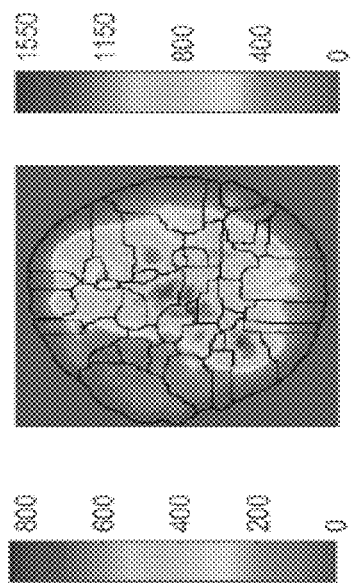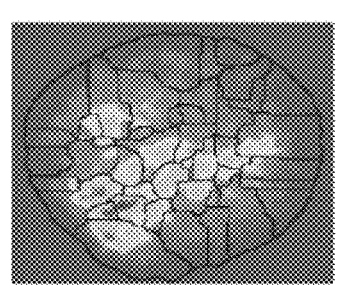
FIG. 14A  FIG. 14B  FIG. 14C  FIG. 14D  FIG. 14E

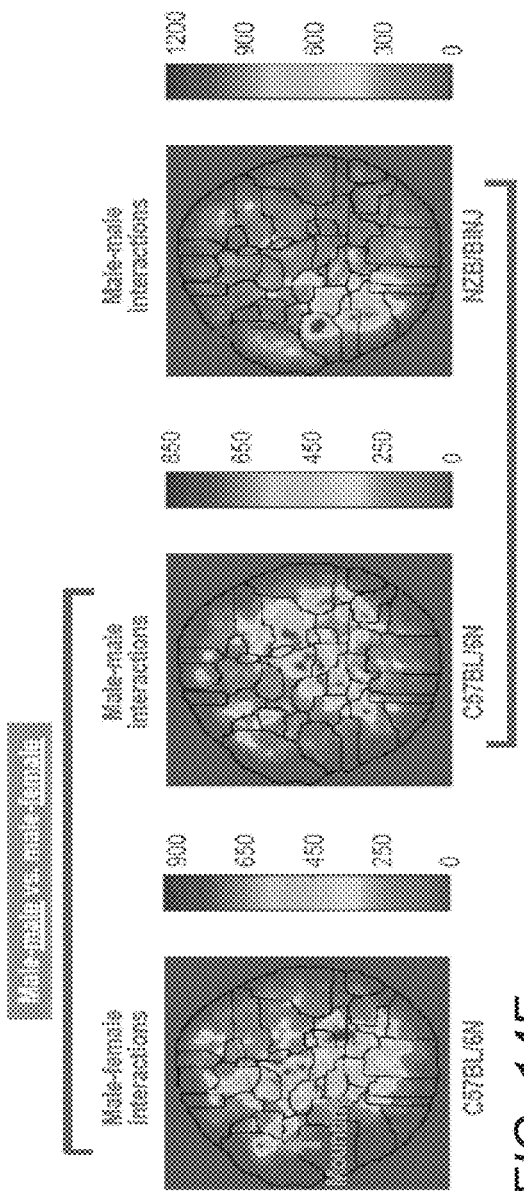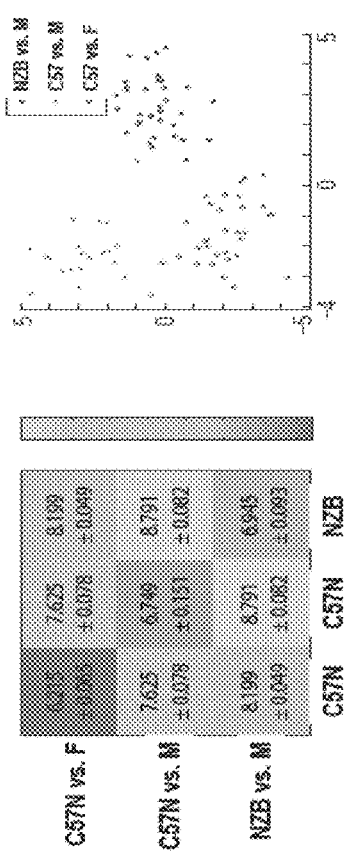
FIG. 14F  FIG. 14G  FIG. 14H  FIG. 14I  FIG. 14J

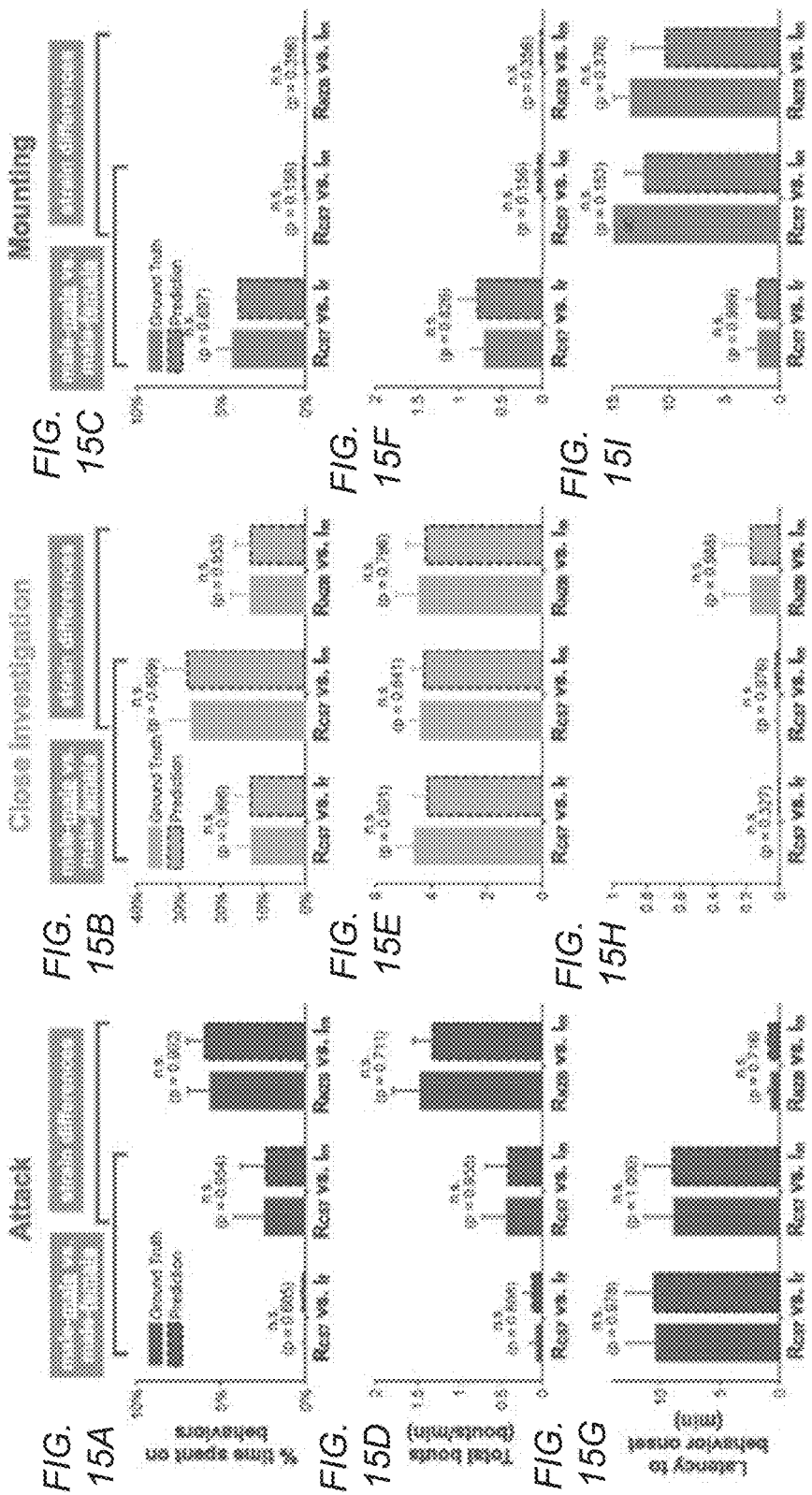

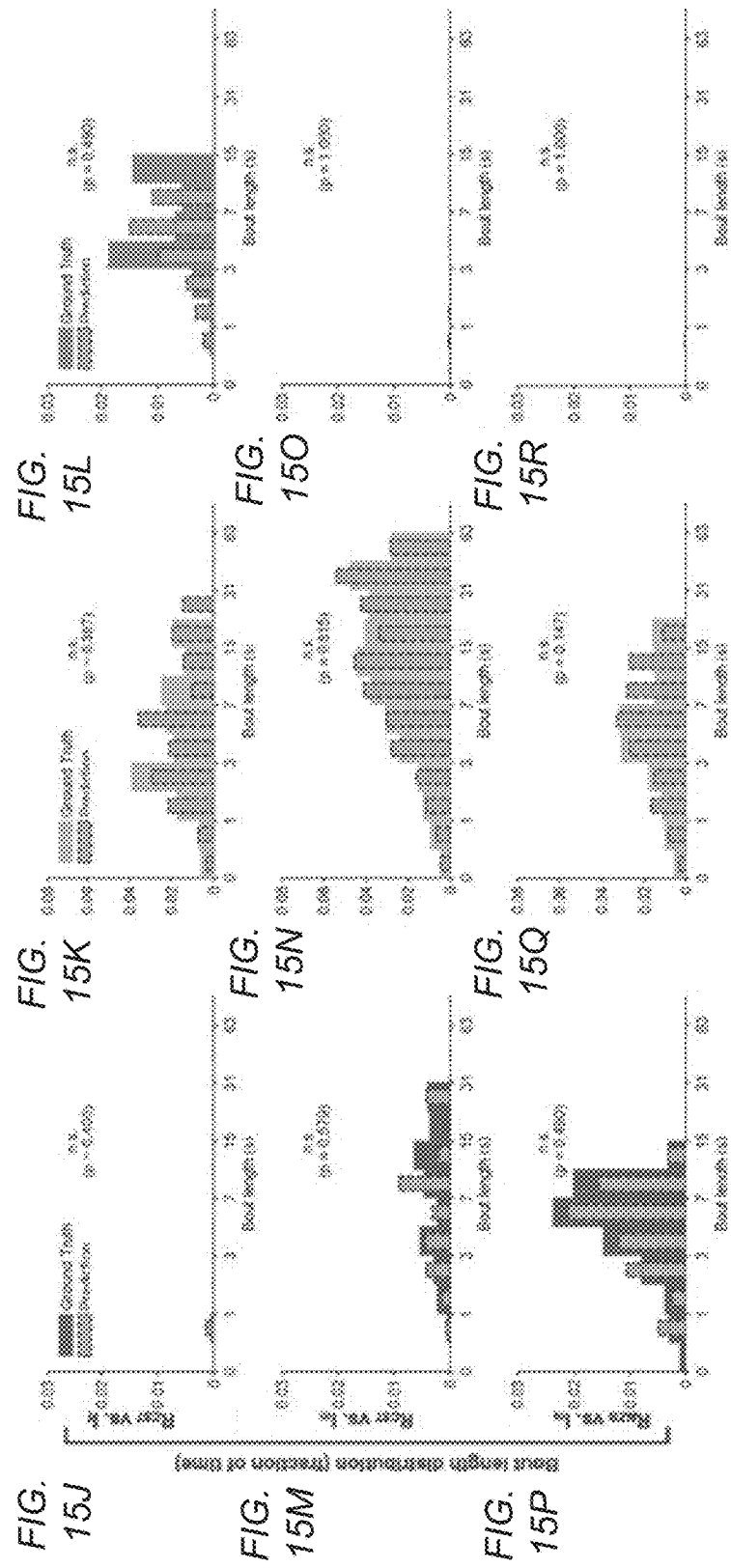

SYSTEMS AND METHODS FOR BEHAVIOR DETECTION USING 3D TRACKING AND MACHINE LEARNING

CROSS-REFERENCE TO RELATED APPLICATIONS

The current application claims priority to U.S. Provisional Patent Application Ser. No. 62/148,663 entitled "Automated Measurement of Mouse Home Cage Social Behaviors Using 3D Tracking and Machine Learning" filed Apr. 16, 2015 and U.S. Provisional Patent Application Ser. No. 62/205,556 entitled "Automated Measurement of Mouse Home Cage Social Behaviors Using 3D Tracking and Machine Learning", filed Aug. 14, 2015. The disclosures of U.S. Provisional Patent Application Ser. Nos. 62/148,663 and 62/205,556 are hereby incorporated herein by reference in their entirety.

FIELD OF THE INVENTION

The present invention generally relates to machine vision systems for performing behavior detection using 3D tracking and machine learning, and more specifically, in some embodiments, to the detection of behavior of multiple subjects using 3D tracking.

BACKGROUND

Social behaviors are critical for animals to survive and reproduce. While many social behaviors are innate, they must also be dynamic and flexible to allow adaptation to a rapidly changing environment. The study of social behaviors in model organisms typically requires accurate detection and quantification of such behaviors. Although automated systems for behavioral scoring in some animal species are available, they are generally limited to single animal assays, and their capabilities are restricted either to simple tracking, or to specific behaviors that are measured using a dedicated apparatus (e.g., to measure freezing during fear conditioning, etc.). However, there is increasing interest in quantifying social behaviors in rodents and other animal species, to study mechanisms and treatments for human psychiatric disorders that affect social interactions. In contrast to single animal behaviors, social behaviors are typically scored manually. This is slow, highly labor intensive and subjective, resulting in analysis bottlenecks as well as inconsistencies between different human observers. The issues associated with having humans attempt to manually score behaviors captured in video sequences is viewed by many as limiting progress toward understanding the function of neural circuits and genes controlling social behaviors, and their dysfunction in disorders such as autism.

SUMMARY OF THE INVENTION

A lack of automated, quantitative, and accurate assessment of social behaviors has limited progress toward understanding mechanisms underlying social interactions and their disorders such as autism. Systems and methods in accordance with various embodiments of the invention utilize integrated hardware and software systems that combine video tracking, depth sensing, machine vision and machine learning, for automatic detection and quantification of social behaviors. In many embodiments, the behavioral classification systems are adapted to detect behaviors involving close and dynamic interactions between two subjects. In several embodiments, the behavioral classification system utilizes hardware that integrates conventional video cameras that capture color or monochrome images with a depth sensor (or "depth camera"). The captured image data that includes depth information is then analyzed via an image processing pipeline, which extracts the body "pose" of individual subjects, and uses supervised machine learning to develop classifiers capable of classifying several well-described social behaviors. Unsupervised machine learning can also be used to gain insights into behaviors that may not be readily apparent based upon human observation.

Systems and methods in accordance with many embodiments of the invention can be utilized in a massively parallel context to enable very high-throughput measurements of the behavior of very large numbers of subjects (e.g. hundreds or thousands of subjects). Such systems can be utilized to ascertain the behavioral impact of administration of pharmaceuticals to subjects. In addition, such systems can be utilized to determine whether specific genotypes (e.g., among a large collection of mutant organisms) and/or experimental treatments (e.g., stress) give rise to a behavioral phenotype and/or the extent to which treatment with a pharmaceutical impacts the behavioral phenotype. In this way, systems and methods in accordance with various embodiments of the invention can offer the ability to study social behavioral disorders in a manner previously not attempted due to the laborious nature of manual annotation of observed behavior. In a number of embodiments, the relationship between behavioral phenotype and genotypes is also utilized to estimate a genotype of a subject based upon detected behavior and/or patterns of detected behavior.

One embodiment of the invention includes: a microprocessor; and memory containing a classification application. In addition, the classification application directs the microprocessor to: identify at least a primary subject interacting with a secondary subject within a sequence of frames of image data including depth information; determine poses for at least the primary subject and the secondary subject within a plurality of frames from the sequence of frames of image data; extract a set of parameters describing the poses and movement of at least the primary and secondary subjects from the plurality of frames from the sequence of frames of image data; and detect a social behavior performed by at least the primary subject and involving at least the second subject using a classifier trained to discriminate between a plurality of social behaviors based upon the set of parameters describing poses and movement of a plurality of subjects extracted from a plurality of frames of image data including depth information.

In a further embodiment, the classifier is trained to discriminate between a plurality of social behaviors using a training data set including a plurality of sequences of frames of image data including depth information.

In another embodiment, each sequence of frames of image data including depth information in the training data set is annotated using one of a predetermined set of a plurality of social behaviors, and the classifier is trained to discriminate between behaviors within the predetermined set of a plurality of social behaviors.

In a still further embodiment, the training of the classifier using the training data set automatically generates a set of a plurality of social behaviors observed in the training data set, and the classifier is trained to discriminate between behaviors within the automatically generated set of a plurality of social behaviors observed in the training data set.

In still another embodiment, the classification application further directs the microprocessor to detect occurrence of modified social behavior in at least the primary subject resulting from administration of a pharmaceutical.

In a yet further embodiment, the classification application further directs the microprocessor to detect a behavioral phenotype associated with a genotype of the primary subject based upon detection of a pattern of social behaviors including the detected social behavior by a set of subjects including at least the primary subject that share the same genotype.

In yet another embodiment, the primary and secondary subjects are rodents.

In a further embodiment again, the plurality of behaviors include a plurality of behaviors selected from the group consisting of: attack, close inspection, mounting, chasing, social grooming, maternal behavior, paternal behavior, female receptivity, and social feeding.

In another embodiment again, the classification application further directs the microprocessor to detect occurrence of modified social behavior in at least the primary subject resulting from administration of a pharmaceutical.

In a further additional embodiment, the classification application further directs the microprocessor to detect a behavioral phenotype associated with a genotype of the primary subject based upon detection of a pattern of social behaviors including the detected social behavior by a set of subjects including at least the primary subject that share the same genotype.

In another additional embodiment, the primary and secondary subjects are non-human primates.

In a still yet further embodiment, the classification application further directs the microprocessor to detect occurrence of modified social behavior in at least the primary subject resulting from administration of a pharmaceutical.

In still yet another embodiment, the classification application further directs the microprocessor to detect a behavioral phenotype associated with a genotype of the primary subject based upon detection of a pattern of social behaviors including the detected social behavior by a set of subjects including at least the primary subject that share the same genotype.

In a still further embodiment again, the classification application directs the microprocessor to identify at least a primary subject interacting with a secondary subject within a sequence of frames of image data including depth information by: performing background subtraction using a plurality of frames of image data; and performing segmentation of at least a primary subject and a secondary subject.

In still another embodiment again, the classification application further directs the microprocessor to identify at least a primary subject interacting with a secondary subject within a sequence of frames of image data including depth information based upon characteristic markings of primary and second subjects visible within frames of image data including video data in at least one color channel.

In a still further additional embodiment, the classifier is selected from the group consisting of a support vector machine, adaptive boosting, and a random decision forest.

In still another additional embodiment, the image data further includes video data in at least one color channel.

A yet further embodiment again also includes: a 3D imaging system. In addition, the classification application further directs the microprocessor to: control the 3D imaging system to acquire the sequence of frames of image data including depth information and video image data in at least one color channel; and store the sequence of frames of image data including depth information in memory.

In yet another embodiment again, the 3D imaging system is selected from the group consisting of:

a time of flight depth sensor and at least one camera;
a structured light depth sensor and at least one camera;
a LIDAR depth sensor and at least one camera;
a SONAR depth sensor and at least one camera;
a plurality of cameras in a multiview stereo configuration; and
a plurality of cameras in multiview stereo configuration and an illumination source that projects texture.

In a yet further additional embodiment, the 3D imaging system further includes an additional camera.

In yet another additional embodiment, the camera is selected from the group consisting of a monochrome camera, a Bayer camera, and a near-IR camera.

In a still yet further embodiment again, the classification application further directs the microprocessor to: extract a set of parameters describing the poses and movement of at least the primary and secondary subjects from the plurality of frames from the sequence of frames of image data and from additional sensor data; and the classifier is trained to discriminate between a plurality of social behaviors based upon the set of parameters describing poses and movement of a plurality of subjects extracted from a plurality of frames of image data including depth information and additional sensor data.

In still yet another embodiment again, the additional sensor data includes at least one piece of sensor data selected from the group consisting of:
audio data;
motion detection data;
pressure sensor data;
temperature data; and
ambient lighting data.

In a still yet further additional embodiment, the classification application further directs the microprocessor to associate the detected social behavior performed by at least the primary subject with measurement data acquired during the time period in which the detected social behavior was observed in the sequence of frames of image data.

In still yet another additional embodiment, the measurement data measures a characteristic of the primary subject selected from the group consisting a physiological characteristic, a psychological characteristic, and a molecular characteristic.

In a yet further additional embodiment again, the measurement data measures neuronal activity.

In yet another additional embodiment again, the classification application further directs the microprocessor to: detect a sequence of a plurality of social behaviors performed by at least the primary subject and involving at least the second subject using the classifier, where the detected behaviors are actions; and identify an activity state of at least the primary subject from amongst a plurality of activity states based upon the detected sequence of a plurality of social behaviors using a classifier trained to discriminate between a plurality activity states based upon a detected sequence of at least one social behavior performed by a subject.

In a still yet further additional embodiment again, the detected social behavior is selected from the group consisting of an action and an activity.

In still yet another additional embodiment again, the classification application directs the microprocessor to detect non-social behaviors performed by at least the primary subject.

In another further embodiment, the detected non-social behaviors are selected from the group consisting of: self-grooming, scratching, digging, circling, walking, running, nesting, freezing, flattening, jumping, thigmotaxis, rearing, risk-assessment (stretched-attend posture), climbing, eating, drinking, burying, and sleeping.

Still another further embodiment includes: a plurality of 3D imaging systems and a behavioral classification computer system including at least one memory and at least one microprocessor directed by at least a classification application stored in the at least one memory to: control the plurality of 3D imaging systems to each acquire a sequence of frames of image data including depth information; and store at least a portion of each of the sequences of frames of image data including depth information in the at least one memory. In addition, for each of the sequences of frames of image data the behavioral classification computer system is configured to: identify at least a primary subject interacting with a secondary subject within a given sequence of frames of image data including depth information; determine poses for at least the primary subject and the secondary subject within a plurality of frames from the given sequence of frames of image data; extract a set of parameters describing the poses and movement of at least the primary and secondary subjects from the plurality of frames from the given sequence of frames of image data; and detect a social behavior performed by at least the primary subject and involving at least the second subject using a classifier trained to discriminate between a plurality of social behaviors based upon the set of parameters describing poses and movement of a plurality of subjects extracted from a plurality of frames of image data including depth information; and store the detected social behavior and an association with the primary subject in the at least one memory.

In yet another further embodiment, the behavioral classification computer system is further directed to detect occurrence of modified social behavior resulting from administration of a pharmaceutical to a set of a plurality of primary subjects identified in the plurality of sequences of frames of image data based upon the detected social behaviors associated with the set of a plurality of primary subjects stored in the at least one memory.

In another further embodiment again, the behavioral classification computer system is further directed to: detect a behavioral phenotype associated with a genotype shared by a set of a plurality of primary subjects identified in the plurality of sequences of frames of image data based upon: the detected social behaviors associated with the set of a plurality of primary subjects stored in the at least one memory; and data describing a genotype of each of the primary subjects identified in the plurality of sequences of frames of image data.

Another further additional embodiment includes: a microprocessor; and memory containing a classification application. In addition, the classification application directs the microprocessor to: identify at least a primary subject interacting with a secondary subject within a sequence of frames of image data including depth information, where the sequence of frames of image data are captured from a viewpoint of the secondary subject; determine poses for at least the primary subject within a plurality of frames from the sequence of frames of image data; extract a set of parameters describing the poses and movement of at least the primary subject from the plurality of frames from the sequence of frames of image data; and detect a social behavior performed by the primary subject and involving at least the secondary subject using a classifier trained to discriminate between a plurality of social behaviors based upon the set of parameters describing poses and movement of a first subject with respect to at least a second subject extracted from a plurality of frames of image data including depth information.

In still yet another further embodiment, the classifier is trained to discriminate between a plurality of social behaviors including aggressive and non-aggressive behaviors; and the detected social behavior performed by the primary subject is an aggressive behavior.

Still another further embodiment again also includes an output device, where the classification application further directs the microprocessor to generate an alert via the output device based upon detection of an aggressive behavior.

Still another further additional embodiment includes: a microprocessor; and memory containing a classification application. In addition, the classification application directs the microprocessor to: identify a primary subject within a sequence of frames of image data including depth information; determine a pose of the primary subject within a plurality of frames from the sequence of frames of image data; extract a set of parameters describing poses and movement of the primary subject from the plurality of frames from the sequence of frames of image data; detect a behavior performed by at the primary subject using a classifier trained to discriminate between a plurality of behaviors based upon the set of parameters describing poses and movement of a subject extracted from a plurality of frames of image data including depth information; and infer a genotype for the primary subject based upon behavior including the detected behavior performed by the primary subject.

In yet another further embodiment again, the classification application further directs the microprocessor to: identify a secondary subject within the sequence of frames of image data including depth information; determine poses for the secondary subject within a plurality of frames from the sequence of frames of image data; and extract a set of parameters describing poses and movement of the primary subject from the plurality of frames from the sequence of frames of image data. In addition, the detected behavior is a social behavior performed by at least the primary subject and involving at least the second subject; and the classifier is trained to discriminate between a plurality of social behaviors based upon the set of parameters describing poses and movement of a plurality of subjects extracted from a plurality of frames of image data including depth information.

BRIEF DESCRIPTION OF THE DRAWINGS

FIGS. 3A-3D illustrate a behavioral classification system including two video cameras and a depth sensor configured to capture image data of at least one mouse in its home cage.

FIG. 4A-4C show side view, top view, and depth sensor image data captured by a behavioral classification system similar to that shown in FIGS. 3A-3D.

FIGS. 6A-6D show image data captured by a top view camera and a depth sensor during a registration process and FIG. 6E shows a MATLAB-generated schematic showing 3D registration of the top view camera and the depth sensor into a common coordinate system.

FIGS. 12A-12F conceptually illustrate features used in 3D tracking accordance with a specific embodiment of the invention.

FIGS. 13A-13D show outputs with respect to male-male interactions, and FIGS. 13E-13F show outputs with respect to male-female interactions.

FIGS. 14A-14J conceptually illustrate identification of clusters of behavior from 3D tracking data using unsupervised learning in accordance with an embodiment of the invention.

FIGS. 15A-15C chart percentage of time resident males spent engaging in attack, mounting, and close investigation of conspecifics.

FIGS. 15D-15F chart measurements made with respect to the total numbers of bouts during recording of image data.

FIGS. 15G-15I chart latency to first bout of behavior for each resident male.

FIGS. 15J-15R chart distribution of bout lengths for each behavior.

DETAILED DISCLOSURE OF THE INVENTION

Figure 1:
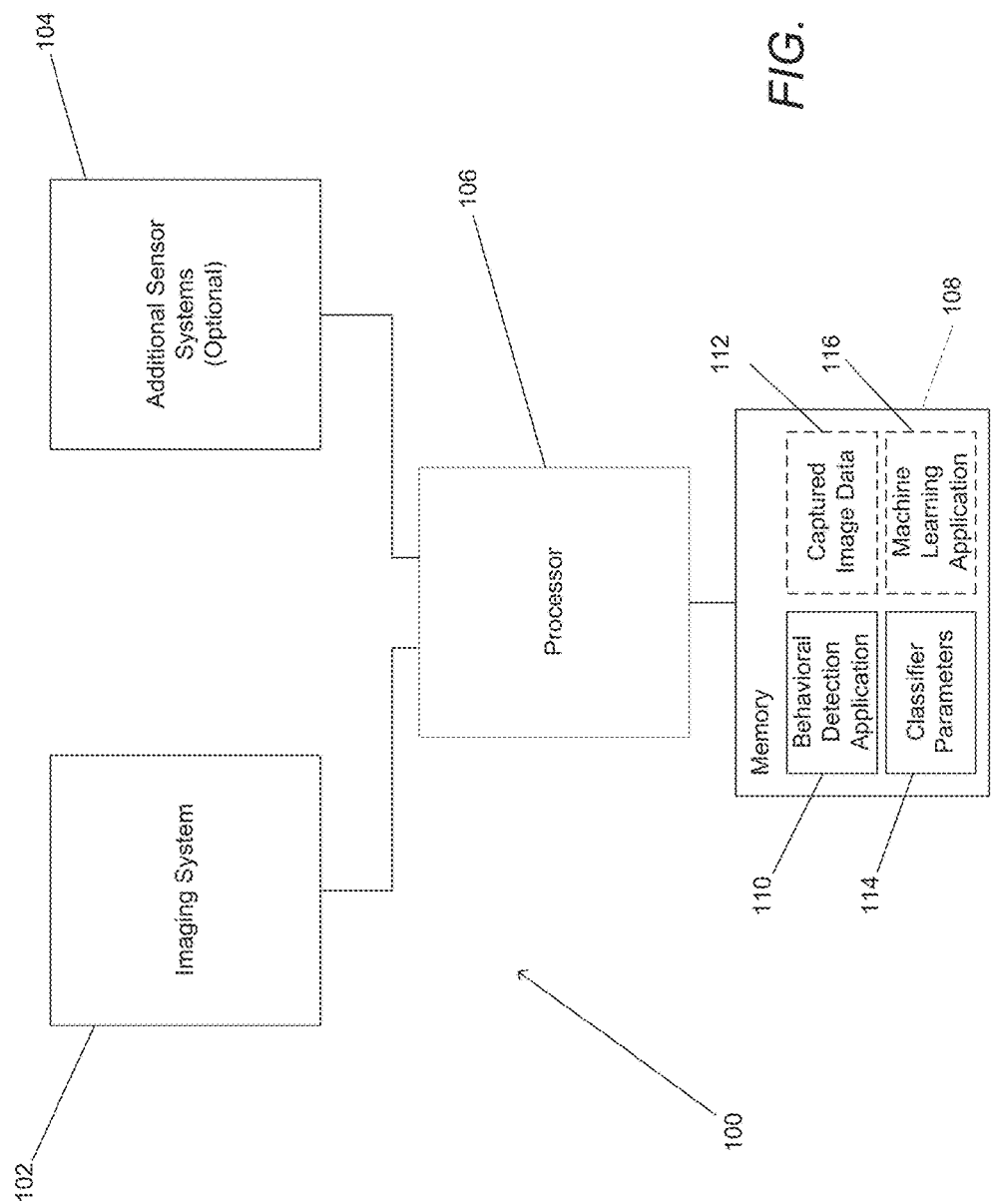
FIG. 1 is a block diagram of a behavioral classification system in accordance with an embodiment of the invention.

Turning now to the drawings, systems and methods for performing behavioral detection using three-dimensional tracking and machine learning in accordance with various embodiments of the invention are illustrated. In many embodiments, a behavioral classification system that incorporates a imaging system designed to capture depth information and intensity information in at least one color channel information is utilized to observe one or more subjects. In several embodiments, the behavioral classification system uses three-dimensional tracking of multiple subjects to detect social behaviors. While much of the discussion that follows relates to the detection of social behaviors, because the detection of such behaviors is extremely valuable in the study of behavioral disorders, behavioral classification systems in accordance with many embodiments of the invention are designed to detect behaviors of a single subject and/or non-social behaviors of multiple subjects (e.g. grooming, freezing, scratching, digging, etc.).

In discussing behavior, it should be appreciated that behaviors can be complex and are often considered as including smaller elements such as (but not limited to) "actions", which are simple elements (e.g. chasing, sniffing or mounting). More complex combinations of actions are often referred to as "activities" (e.g., "aggression" or "mating"). The term "behavior" is used by many machine vision experts to encompass both "actions" and "activities". While much of the discussion that follows involves experiments in which classification of observed actions can be useful in identifying specific activities (e.g. aggressive, close social investigation, and/or mating), behavioral classification systems in accordance with various embodiments of the invention are not limited to classification of actions. Classifiers utilized in behavioral classification systems in accordance with a number of embodiments of the invention can be trained to classify activities. Accordingly, the discussion that follows uses the term behavioral classification generally and behavioral classification systems and behavioral classification processes in accordance with embodiments of the invention are not limited with respect to the granularity of the behaviors that are classified.

In many embodiments, behavioral classification systems can classify social behaviors using image data of a single subject interacting with an unseen second individual. Behavioral classification systems that can classify social behaviors in this way can be particularly useful in a first responder context to provide contextually relevant information and/or alerts to first responders of potentially threatening behavior and/or an impaired state of a particular person with whom the first responder is interacting. Beyond simply classifying an observed behavior, classification of behavior over time can be useful in the analysis of more complex behaviors including (but not limited to) detection of high level goals, high level behaviors, and observation of patterns of behavior exhibited by subjects having specific behavioral disorders.

In a number of embodiments, behavioral classification systems can be utilized to observe behavior of a very large number of subjects. Such systems can be referred to as high-throughput behavioral classification systems. In the past high-throughput social behavioral classification has been practically infeasible. Conducting a behavioral study of 10,000 pairs of mice that are each observed for 20 minutes is estimated to take approximately 5 or more person years to manually annotate the resulting captured video data. A high-throughput behavioral classification system in accordance with an embodiment of the invention could analyze the same amount of video in a fraction of the time depending upon the extent of the parallelization of the process. Indeed, completion of a study of 10,000 pairs of mice (e.g., each exposed to a different drug) within two to three weeks using a high-throughput behavioral classification system observing 500 pairs of mice at a time is realistic. Data collected by high-throughput behavioral classification systems can be utilized for purposes including (but not limited to) pharmaceutical screening, observation of behavioral phenotypes associated with specific genotypes, and/or effectiveness of pharmaceuticals on treating specific behavioral phenotypes or measuring their behavioral side-effects. Where relationships between genotypes and specific behavioral phenotypes can be established, systems and methods in accordance with a number of embodiments of the invention can utilize detected behavior and/or patterns of detected behavior to estimate a genotype of a subject based upon detection of a behavioral phenotype.

Behavioral classification data generated by behavioral classification systems in accordance with various embodiments of the invention can also be combined with additional behavioral and/or non-behavioral measurement data to gain insights into the relationships between the measurements and the behavior of the subject. For example, time stamped measurements of neuronal activity (e.g., using electrophysiological recording or functional imaging) can be synchronized with detected behaviors to develop insights into the relationships between particular patterns of neuronal activity and specific behavioral phenotypes. Such an approach can be used to investigate how brain activity is altered in response to e.g., a drug of abuse or genetic mutation that produces a particular behavioral phenotype, thereby suggesting potential routes towards treatment. As can readily be appreciated, any of a variety of data sources and/or measurements can be synchronized with behavioral classification data generated in accordance with various embodiments of the invention as appropriate to the requirements of a specific application.

In a number of embodiments, detection of behaviors is performed using a classifier trained using one of a number of appropriate machine learning techniques. In several embodiments, the classifier is trained using a supervised and/or semi-supervised learning technique in which a training database of recorded image data (including depth information) that is manually annotated with a predetermined set of behaviors (so-called "ground truth") is utilized to train the classifier. In other embodiments, an unsupervised learning technique is utilized in which a machine learning process categorizes/classifies different behaviors automatically from an unannotated training data set. The resulting set of behaviors may or may not correspond to behaviors previously categorized by human observers, and, in this way, can provide insights into the behaviors of the subject(s) that may not have been previously detected. This approach could be used, for example, to identify different categories of subtle or unsuspected behavioral side-effects produced by different drugs with similar therapeutic targets. While much of the discussion that follows describes performing classification based upon image data including image data captured by one or more conventional video cameras, as well as depth sensors, classifiers in accordance with many embodiments of the invention can be trained to perform classification based upon image data and additional modalities as appropriate to the requirements of a specific behavioral classification application. Behavioral classification systems and methods for performing behavioral classification in accordance with various embodiments of the invention are discussed further below.

Behavioral Classification Systems

A behavioral classification system in accordance with an embodiment of the invention is illustrated in FIG. 1. The behavioral classification system 100 includes a imaging system 102 that is capable of capturing image data including depth information. Depth information typically refers to a measurement of a distance from a reference viewpoint to one point or many points in a scene. In many embodiments where a camera is used to acquire images of one or more subjects and a separate depth sensor is used to acquire depth information either the data captured by the conventional camera is registered with respect to the viewpoint of the depth sensor or the raw depth information is warped into the viewpoint of a conventional camera. While not strictly necessary, subsequent analysis of the image data can be simplified when at least a portion of the image data is registered with respect to a common viewpoint. As is detailed further below, use of depth information can offer several unique advantages over the use of traditional 2D video analysis alone. Depth information can improve detection of a subject's body orientation (or "pose"), and provided better detection of vertical movements that can be relevant to some behaviors.

Depth information can be obtained using any of a variety of depth sensors including (but not limited to) a time of flight depth sensor, a structured illumination depth sensor, a Light Detection and Ranging (LIDAR) sensor, a Sound Navigation and Ranging (SONAR) sensor, an array of two or more conventional cameras in a multiview stereo configuration, and/or an array of two or more conventional cameras in a multiview stereo configuration in combination with an illumination source that projects texture onto a scene to assist with parallax depth information recovery on otherwise textureless surfaces. As can readily be appreciated, the specific depth sensor utilized to obtain depth information largely depends upon the requirements of a specific application.

In addition to depth information, the imaging system 102 can include one or more conventional cameras that are utilized for the purpose of capturing image data related to the intensity of portions of the electromagnetic spectrum including (but not limited to) portions of the visible spectrum, the near-Infrared spectrum, and Infrared (IR) spectrum. In certain embodiments, cameras utilized in the imaging system 102 are (but are not limited to) monochrome cameras that may optionally include an IR cut filter, cameras that incorporate Bayer filters to image in the Red, Green, and Blue color channels, and/or cameras that employ any of a variety of color filters to image in a single or multiple color channels as appropriate to the requirements of a given behavioral classification application. For the purposes that follow, image data is utilized to refer to both information concerning intensity in one or more color channels and depth information. In many applications, image data take the form of so called RGB-D data (i.e. Red, Green, Blue, and Depth image data). The specific image data output by a imaging system utilized in a behavioral classification system in accordance with an embodiment of the invention is largely dependent upon the requirements of a particular behavioral classification application.

As is discussed further below, the use of depth information as an additional modality in combination with conventional video data can significantly enhance the accuracy and robustness of automated behavioral classification processes. Improvements can also be obtained by adding further imaging modalities as inputs to behavior classification processes in accordance with many embodiments of the invention. Accordingly, behavioral classification systems in accordance with a number of embodiments of the invention also include one or more additional sensor systems 104 that provide information that can be utilized in performing behavioral classification. The additional sensor systems 104 can include (but are not limited to) audio data, motion detection data, pressure sensor data, temperature data, and/or ambient lighting data. As can readily be appreciated, the specific additional sensor systems utilized by a behavioral classification system in accordance with various embodiments of the invention largely depends upon the requirements of a given application.

In the embodiment illustrated in FIG. 1, the imaging system and the (optional) additional sensors provide data to a computer system that performs behavioral classification. The computer system includes a processor 106 that receives image data including depth information from the imaging system 102 and/or information from (optional) additional sensor systems 104. As is discussed further below, the processor system is shown as receiving the data directly from the imaging system 102 and/or (optional) additional sensor systems 104. In many embodiments, the data are not transferred in real time and may be transferred by physical movement of a storage device containing the large quantities of image data that can be generated during an extended observation of one or more subjects. In a number of embodiments, data is transferred to cloud storage and may be processed either immediately upon uploading or at a later time by a cloud service that makes the results of the analysis available to a user that maintains an account with the cloud service. The processor 106 shown in FIG. 1 can be any of a variety of different processor architectures including (but not limited to) one or more central processing units (CPU), one or more cores of a CPU, one or more graphics processing units (GPUs), and/or one or more digital signal processing (DSP) units. In other embodiments, the processor can incorporate application specific integrated circuits such as (but not limited to) field programmable gate arrays (FPGAs). As such, the processor should not be considered as limited to a single device but can be implemented using one or more devices that cooperate to provide the computational capabilities for performing the various behavioral classification processes discussed in detail below.

Machine readable instructions stored in memory 108 can be used to control the operations performed by the processor 106. In the illustrated embodiment, a behavioral detection application 110 is stored in memory 108. The behavioral detection application 110 directs the processor to perform a number of image processing applications designed to track one or more subjects in the captured image data 112 in 3D. The behavioral detection application 110 can extract features that describe the 3D tracked subjects in a manner that enables behavioral classification with high reliability. The behavioral detection application 110 can utilize the processor to implement one or more behavioral classifiers using classifier parameters 114 retrieved from memory 108. In a number of embodiments, the behavioral classifiers can detect social behaviors including (but not limited to) attack, close inspection, mounting, chasing, social grooming, maternal behavior (pup-gathering, licking/grooming), paternal behavior (pup-gathering), Female receptivity (lordosis), and/or social feeding. In several embodiments, the behavioral classifiers can detect non-social behaviors including (but not limited to) self-grooming, scratching, circling, walking, running, digging, nesting, freezing, flattening, jumping, thigmotaxis, rearing, risk-assessment (stretched-attend posture), climbing, eating, drinking, burying (e.g., marbles or probes), and/or sleeping. In other embodiments, behavioral classifiers can detect any of a variety of social and/or non-social behaviors as appropriate to the requirements of a given application.

As is discussed further below, machine learning processes can be utilized to determine the classifier parameters 114. In a number of embodiments, the behavioral classification system includes a machine learning application 116 that performs on-line learning by periodically directing the processor to retrain the one or more classifiers using captured image data 112. In several embodiments, the machine learning application 116 utilizes unsupervised learning processes to automatically train one or more of the classifiers. In a number of embodiments, the machine learning application 116 utilizes supervised learning to train one or more of the classifiers and generates an interactive user interface (or offloads the recorded image data to a cloud service that generates in interactive user interface) to prompt a user to annotate one or more sequences of image data to continuously expand a training data set of ground truth data for the purposes of training the one or more classifiers. As can readily be appreciated, the specific applications and/or data resident within the memory of a behavioral classification system in accordance with various embodiments of the invention is largely dependent upon the requirements of a given application.

While the embodiment shown in FIG. 1 involves a computer system processing data that is directly provided by a imaging system and/or additional sensors, in many embodiments data is stored and transferred to a computer system that processes the data. For example, in many of the high-throughput systems describe below image data and/or other measurements are recorded to a storage device. The amounts of data involved can be extremely large and the simplest mode for transferring the data to a computer system may be physical transportation of a removable storage devices such as (but not limited to) a portable magnetic disk, or solid state hard drive. In certain embodiments, data is communicated from the imaging systems via a network to a server system that processes the data in real time or as a batch process. As can readily be appreciated, the specific architecture utilized to transfer data captured by one or more imaging systems and/or one or more additional sensor systems to one or more computer systems to perform automatic behavior detection in accordance with various embodiments of the invention largely depends upon the requirements of a specific application. Processes for automatically performing behavior detection in accordance with a number of embodiments of the invention are discussed further below.

Behavioral Classification Using 3D Tracking

Behavioral classification systems in accordance with various embodiments of the invention perform behavioral classification by performing 3D tracking of one or more subjects. In several embodiments, position and pose information is passed through a set of feature extractors to obtain a low-dimensional representation from which machine learning algorithms can be used to train classifiers to detect specific behaviors. In other embodiments, the raw position and pose information can be passed directly to the classifier. Using feature extraction, however, can remove uninformative sources of variability from the raw video data and reduce susceptibility of the classifier to overtraining, producing automated behavioral annotations that are accurate and robust. In several embodiments, supervised learning is utilized to detect behaviors that are recognizable by human observers. In many embodiments, unsupervised learning is utilized to detect clusters of behaviors that provide meaningful information concerning the behavior of subjects that may not have otherwise been readily apparent to a human observer.

Figure 2:
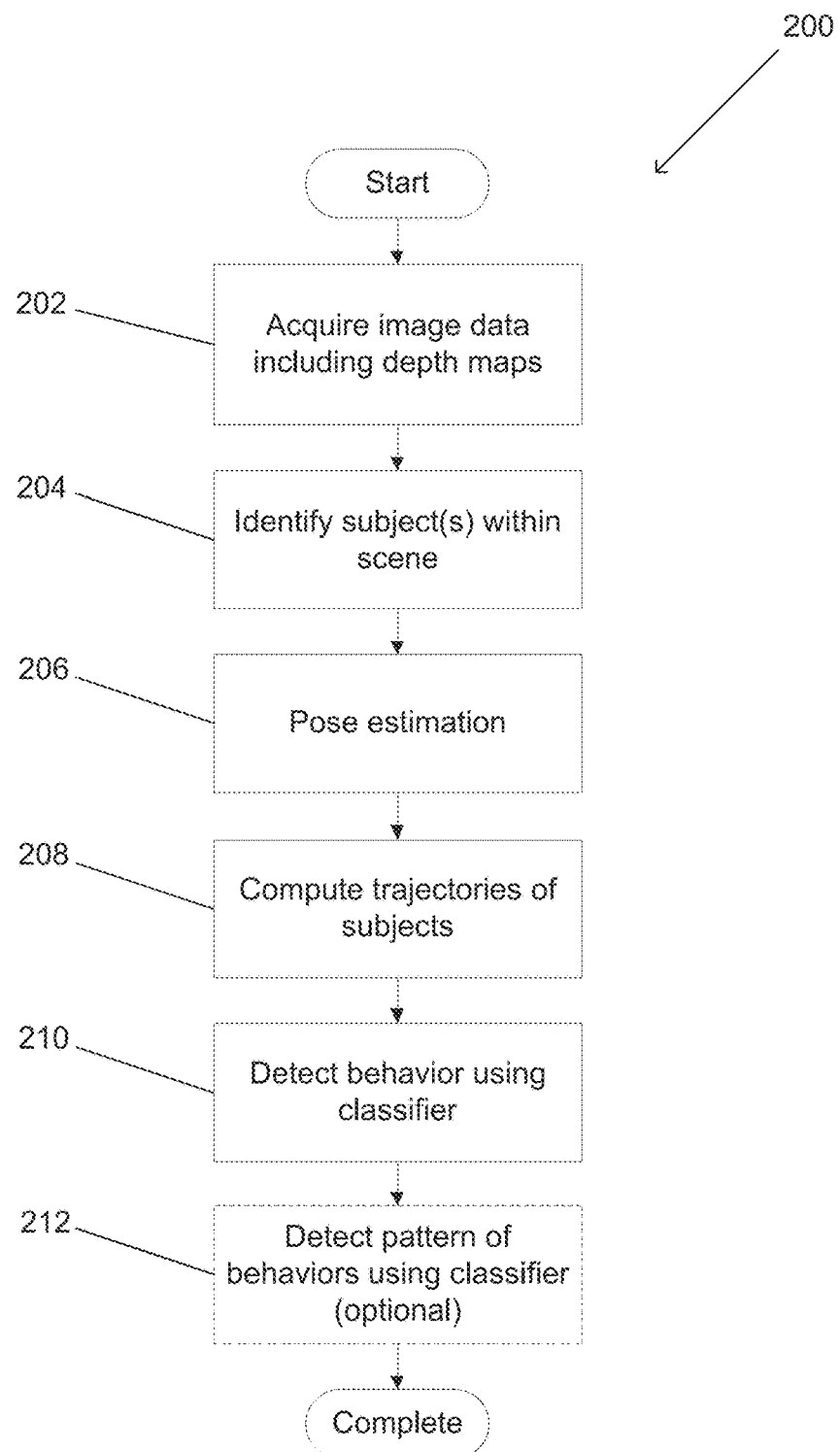
FIG. 2 is a flow chart illustrating a process for performing behavioral classification using 3D tracking in accordance with an embodiment of the invention.
Figure 3B:
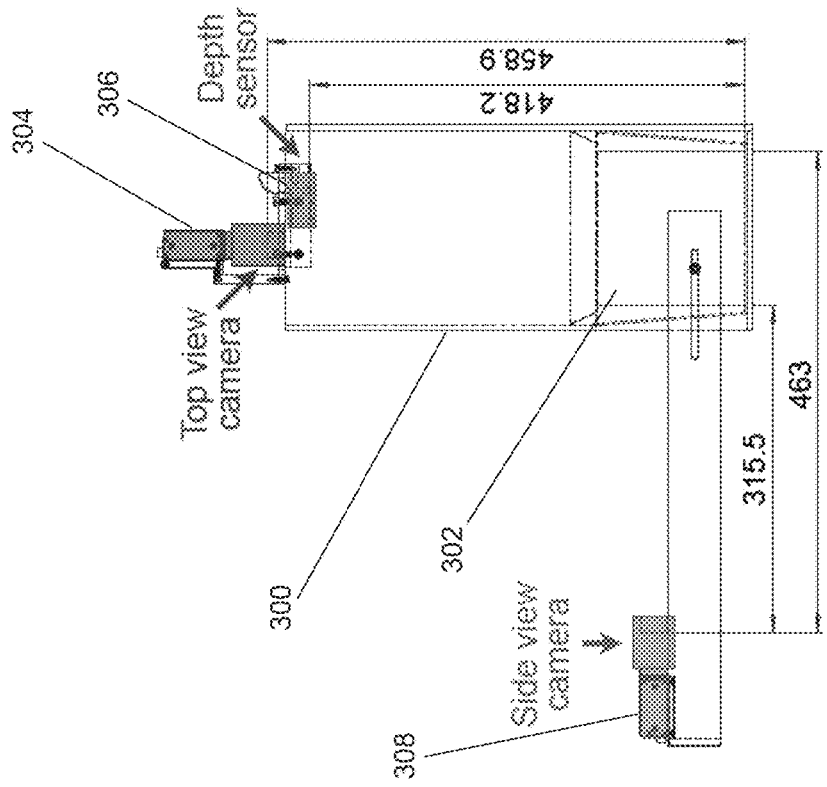
Figure 3A:
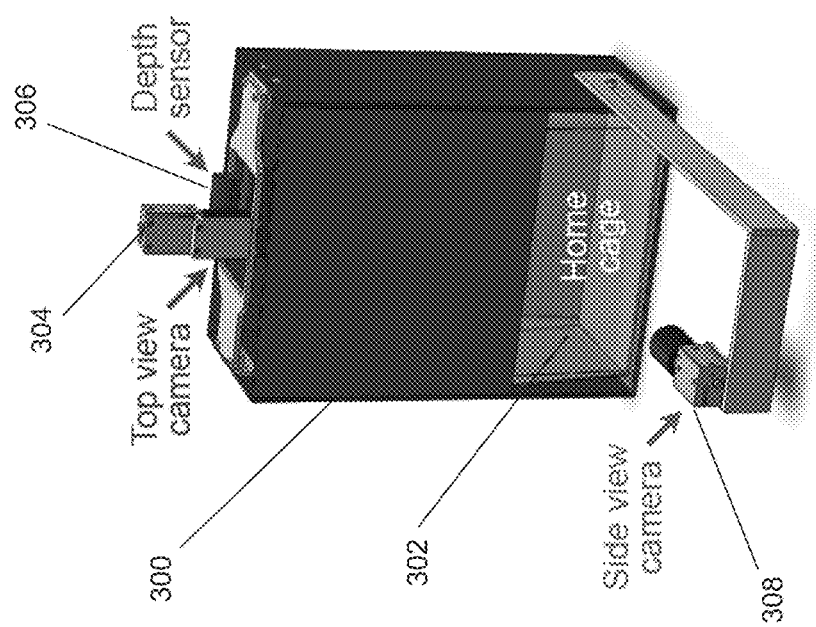

A process for performing behavior detection using 3D tracking in accordance with an embodiment of the invention is illustrated in FIG. 2. The process 200 includes acquiring (202) image data including depth information. One or more subjects are identified (204) within the individual frames of image data and the pose of the identified subjects determined (206). Utilizing pose information across a sequence of frames, the subjects can be tracked in 3D over time. As noted above, classifier performance can be enhanced by extracting (208) a low dimensional feature set that enables classifiers utilized in accordance with different embodiments of the invention to achieve high levels of discrimination between different types of behavior. Various feature sets that can be utilized in specific applications are discussed in more detail below, but it should be appreciated that behavioral classification systems in accordance with embodiments of the invention are not limited to the use of any specific feature set. The specific choice of feature set is largely determined by the captured image data and the requirements of a given application. In other embodiments, classification can be performed based upon raw image data, detected pose and raw 3D trajectory information, and/or any combination of raw data, pose data, trajectory data, and/or parameters appropriate to the requirements of a specific application.

In the process 200 shown in FIG. 2, a set of parameters that forms a low dimensional representation of the tracked subjects in 3D is provided to a set of one or more classifiers that discriminate (210) between one of a number of different behaviors (including a "no behavior of interest state"). Many of the behavioral classification systems described below utilize the detected behaviors to generate an output (e.g. alerting a user to detection of aggressive behavior). In several embodiments, the detected behaviors are utilized to perform high level behavior analysis. For example, a sequence of detected behaviors may be provided to one or more classifiers trained to detect (212) patterns of behavior related to higher level objectives (e.g. a subject attempting to achieve a goal such as, but not limited to, defending territory, or mating), or the manifestation of a specific behavioral phenotype. As can readily be appreciated, the uses to which detected behavior data can be applied are varied and many applications involving the use of detected behavior data are discussed in detail below.

Use of Behavioral Classification Systems to Detect Social Behavior in Mice

The manner in which behavioral classification systems can be utilized in the classification of behaviors and specifically in the challenging task of classifying social behaviors by tracking multiple subjects in 3D can be illustrated by considering experimental results obtained using a specific behavioral classification system designed to detect social behaviors in pairs of mice that are tracked using depth information. Social behaviors are considered especially hard to quantify, because they require separating and maintaining the identities, positions and orientations of at least two different subjects, during close and dynamic interactions. This is made particularly difficult by occlusion when the subjects are close together—and most social behaviors in mice occur when the animals are in proximity to each other. In the case of mice, social behavioral assays are ideally performed in the home cage, where bedding absorbs familiar odors and allows digging, nesting and other activities. The fact that bedding is textured and may be rearranged by the mice presents additional challenges for object-background discrimination, tracking and pose estimation. The ability of the behavioral classification system discussed below to observe a mouse in its home environment is particularly relevant to behavioral classification, because removing the mouse from its home cage to a novel, bare cage that is specifically designed to facilitate machine vision algorithms introduces a source of stress to the mouse. In applications such as (but not limited to) pharmaceutical screening, results can be biased due to aberrations in behavior that may be the result of stress and not a product of administration of the pharmaceutical.

A major advantage of the behavioral classification system utilized to obtain the experimental data discussed below is the increased throughput and decreased labor-intensiveness of performing the behavioral classification. Behavioral classification systems similar to the behavioral classification system described below can reduce time requirements for analysis to an initial commitment of several hours to manually generate a training set of annotations and a few minutes to train the classifier, after which large numbers of additional videos can be scored in a matter of minutes. This not only eliminates major bottlenecks in throughput, but can improve the statistical power of behavioral studies by enabling larger sample sizes; this is often a problem for behavioral assays which typically exhibit high variance. Methods of behavior detection in accordance with various embodiments of the invention also open up the possibility of using behavioral assays as a primary, high-throughput screen for drugs or gene variants affecting mouse models of disorders that involve aberrant social interactions, such as (but not limited to) autism, Schizophrenia, depression, anxiety, and/or PTSD.

While the discussion of using behavioral classification systems to detect social behavior in mice is only one of many possible ways in which behavioral classification systems in accordance with embodiments of the invention can be utilized, the example aptly illustrates the effectiveness of behavioral classification systems in detecting social behavior in multiple subjects that are small and exhibit behaviors that involve rapid movement. Furthermore, the example highlights how data collected using behavioral classification systems can be utilized to characterize behavioral phenotypes associated with a specific genotype of observed subjects. As such, experiments involving the use of behavioral classification systems to detect social behavior in mice validate the effectiveness of using behavioral classification systems in accordance with various embodiments of the invention to perform screening of pharmaceuticals, and/or as a diagnostic tool to assist with detection of a genotype that may be associated with an observed behavioral phenotype in any species of subject. Accordingly, similar behavioral classification systems can be more generally adapted for use in performing behavioral detection with respect to rodents. In addition, modifications to the described pose estimation processes involving fitting skeletons to observed subjects can be used in behavioral classification systems designed to classify the behaviors (including social behaviors) of any of a number of endoskeletal animals including additional rodent species (e.g., rats, hamsters, guinea pigs), non-human primates and/or humans. Accordingly, behavioral classification systems in accordance with various embodiments of the invention are not limited to detection of specific types of behavior and/or detection of behaviors exhibited by specific species of subjects. The examples discussed below with respect to mice are readily generalizable through use of appropriate pose estimators and training data sets to any of a variety of behaviors in any of a number of different endoskeletal animals.

Behavioral Classification Systems for Detecting Social Behavior in Mice

Most current mouse tracking systems utilize 2D video. 2D video analysis can have several limitations, such as difficulty resolving occlusion between animals, difficulty detecting vertical movement, and poor animal tracking performance against backgrounds of similar color. To overcome these problems, a behavioral classification system in accordance with an embodiment of the invention was constructed that records behavior using synchronized conventional video cameras and a time-of-flight depth sensor. The behavioral classification system is illustrated in FIGS. 3A-3D.

The behavioral classification system 300 is designed to enable insertion of the home cage 302 of one of the observed mice (referred to as the resident) into the field of view of the imaging system. During an observation, a second mouse (referred to as the intruder) is introduced into the resident mouse's cage and different social behaviors are automatically detected as the mice interact. As is discussed below, the behavioral classification system includes a imaging system incorporating a top view camera 304 mounted above the cage, a depth sensor 306 mounted above the cage and a side view camera 308 mounted to the side of the cage. The imaging system captures image data that is utilized to track two mice within the cage 302 in 3D. Videos taken from the side view and top view cameras provided additional and complementary data, such as luminosity, for post-acquisition image analysis and behavior analysis, and allow users to manually inspect and score behaviors from different angles. During image data capture, data is acquired synchronously by all three devices to produce simultaneous depth information and top and side view grayscale videos. Representative video frames from each of the three devices during three social behaviors (close investigation, attack, and mounting) are shown in FIGS. 4A-4C.

Mice are nocturnal animals, and exposure to white light can disrupt their circadian cycle. Therefore, animal behaviors are advantageously recorded under red light illumination, which is considered "dark" for mice, as mice cannot perceive light within the red to infrared spectrum. Both video cameras and the depth sensor work under red light and do not rely on white light illumination. Because the depth sensor is able to detect mice by their height alone, the behavioral classification system illustrated in FIGS. 3A-3D works under red light illumination, is insensitive to background colors, and is particularly useful in more natural environments such as home cages. This is helpful in studying social behavior, as removing an animal from its home cage for recording or exposing animals to white light illumination heightens stress and affects behavior. In many embodiments, tracking and classifying two mice in a manner that preserves animal indentities is enhanced by using mice having different coat colors. In other embodiments, a similar benefit can be achieved by applying fiducial markers to the mice. The fiducial markers can be applied as stains to the coats of the mice or markers affixed to the mix (e.g. RFID tags, collars, and/or IR sources).

In the illustrated experimental apparatus, the top view camera 304 and the depth sensor 306 are mounted as close together as possible (see FIG. 3D) to limit occlusions (i.e. pixels in the images captured by the top view camera for which depth information is not available due to the occlusion of that pixel location in the field of view of the depth camera). In the illustrated embodiment, the depth sensor is a time-of-flight depth sensor that includes an IR illumination source 320 and an IR camera 322 and detects contours of objects in the depth or z-plane by measuring the time-of-flight of an infrared light signal generated by the IR illumination source 320 between the depth sensor and object surfaces for each point of the depth image generated by the time-of-flight depth sensor, in a manner analogous to SONAR. The specific depth sensor utilized is the Senz3D depth and gesture sensor from Creative Technology Ltd. of Jurong East, Singapore. The Senz3D sensor is designed for a close working range (15-50 cm). Other depth sensors could be utilized to obtain depth information such as, but not limited to, a plurality of cameras configured to capture information in color channels including the near-IR color channel in a multiview stereo configuration in combination with an illumination source configured to project texture onto the scene. As noted above, the specific imaging system utilized in a behavioral classification system in accordance with an embodiment of the invention is largely dependent upon the requirements of a given application.

The behavioral classification system illustrated in FIGS. 3A-3D can be used to track animal trajectories and orientations in 3D in the context of an animal's home cage and detect specific social behaviors, including attack, mounting and close investigation in different orientations (head-to-head, head-to-tail, head-to-side, etc). As is discussed further below, the image data captured by the behavioral classification system can be used to significantly improve upon existing methods for behavior tracking and classification, which typically do not work well when pairs of mice are in close contact or partially overlapping, and/or do not provide specific behavior classification such as attack. The ability of the behavioral classification system to perform automated behavior scoring can greatly facilitate study of the neural circuits, genes and environmental factors that regulate social behavior. Processes for classifying various behaviors of mice including (but not limited to) social and non-social behavior of pairs of mice and the use of the detected behavior data in studying physiological aspects of the subjects in accordance with various embodiments of the invention are discussed further below.

Processes for Detecting Social Behavior in Mice

The behavioral classification system illustrated in FIGS. 3A-3D is capable of annotating behaviors observed in the synchronized image data at three levels: 1) simple video tracking, which locates the centroid of an ellipse fit to each mouse in each frame; 2) pose estimation, which combines information from the video and depth camera recordings to determine the orientation (head vs. tail), height and other postural features of each mouse relative to the other; and 3) automated behavioral detection and scoring using classifiers trained using machine learning techniques. During experiments involving control C57BL/6N mice and BTBR mice (a previously reported genetic autism model), tracking analysis alone was often incapable of detecting differences in the frequency of social interactions. Application of the pose estimator, by contrast, detected a significant difference between strains, as did the automated behavior classifiers. The classifier also provided additional metrics, such as investigation bout length distribution, that were not available from the pose estimator. These data suggest that behavioral classification systems in accordance with various embodiments of the invention may be useful for detecting and quantifying subtle differences in social behavior phenotypes caused by genetic or neuronal circuit-level perturbations (e.g., optogenetics or pharmacogenetics).

Figure 5:
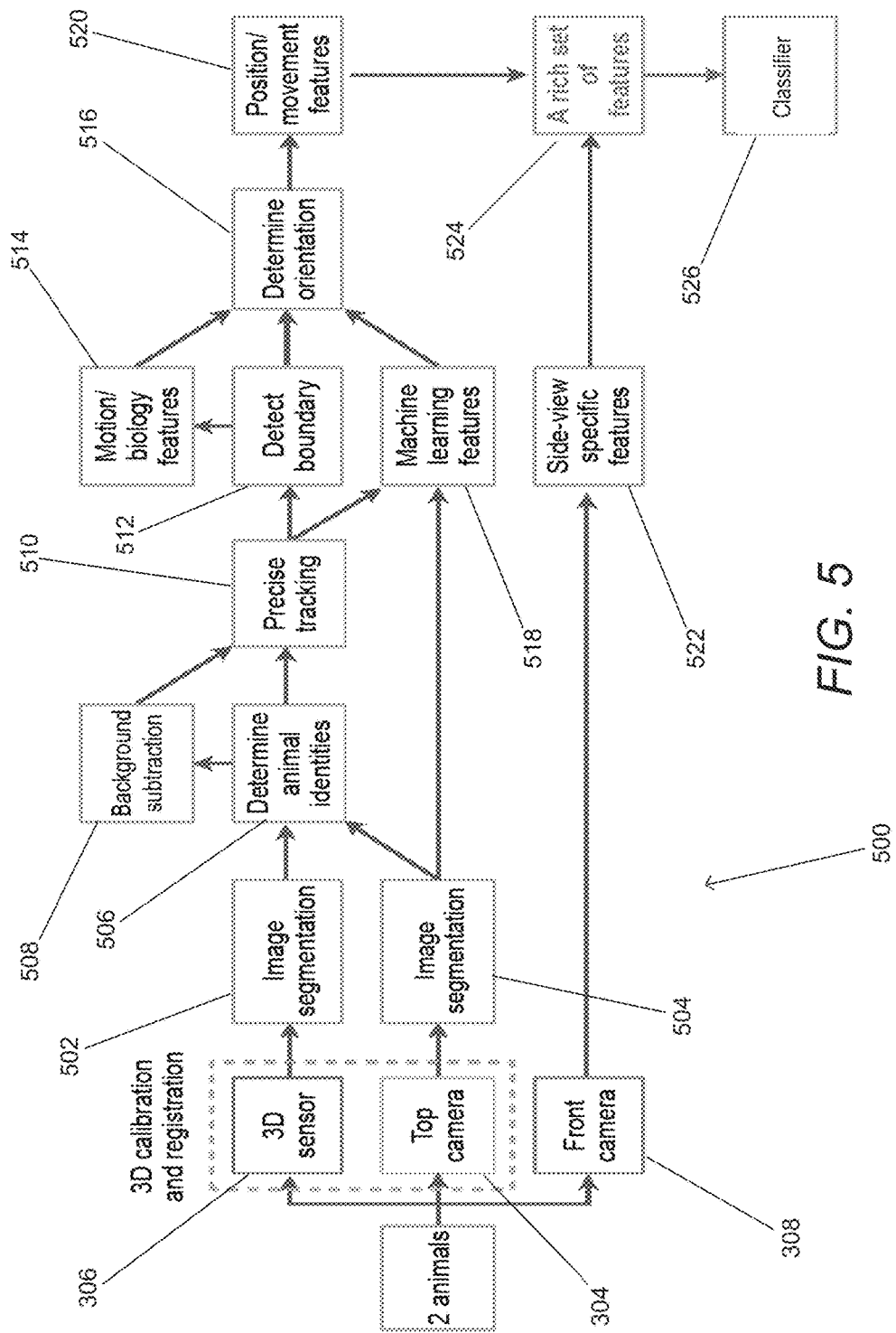
FIG. 5 is a flow chart illustrating a process for performing behavioral classification using image data acquired by a behavioral classification system similar to that shown in FIGS. 3A-3D in accordance with an embodiment of the invention.
Figure 6B:
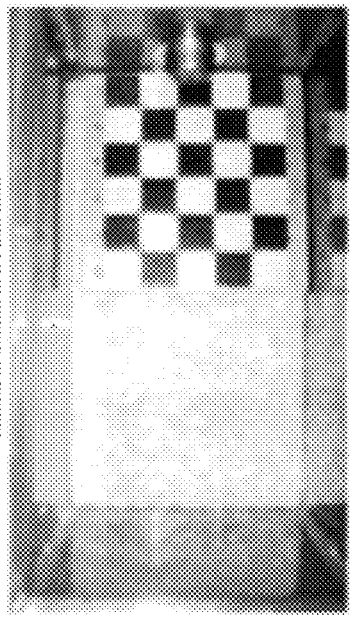
Figure 6D:
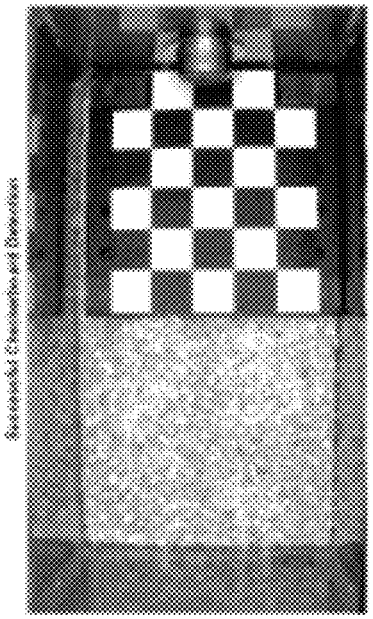
Figure 6A:
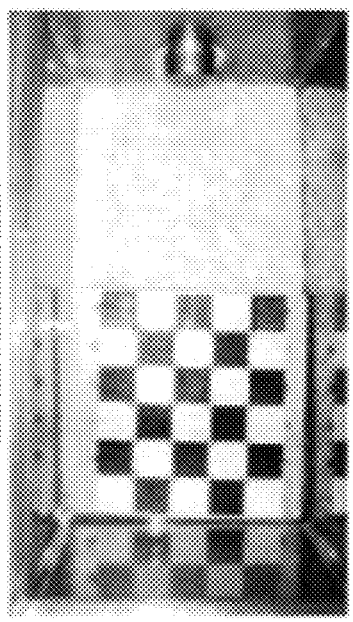
Figure 6C:
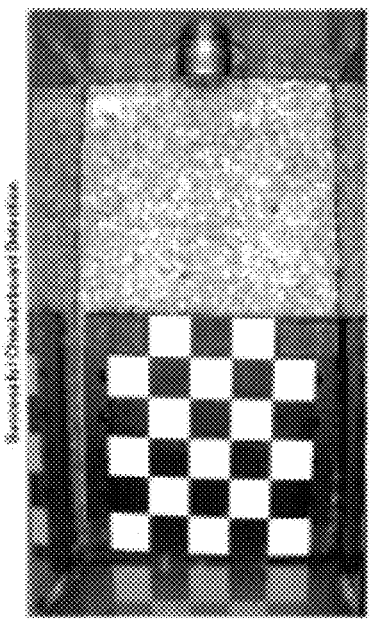

A flow chart illustrating an image processing pipeline implemented by the behavioral classification system illustrated in FIGS. 3A-3D is shown in FIG. 5. The image processing pipeline 500 involves capturing synchronized image data of two animals (e.g. a resident and an intruder) using the top view camera 304, depth sensor 306, and the side view (front) camera 308. The monochrome video recordings from the top view camera are projected into the viewpoint of the depth information captured by the depth sensor to create a common coordinate framework.

The scene independent geometric shifts used to register the monochrome image data with the depth information can be determined using the stereo calibration procedure from MATLAB's Computer Vision System Toolbox, in which a planar checkerboard pattern is used to fit a parameterized model of each camera as illustrated in FIGS. 6A-6D. The top view video frames can then be projected into the coordinate system of the depth sensor to obtain simultaneous depth and intensity values for each pixel (resolutions may also differ). A MATLAB-generated schematic showing 3D registration of the top view camera 304 and the depth sensor 306 into a common coordinate system is shown in FIG. 6E. Locations of checkerboard patterns used for calibration are shown in the upper left portion of the schematic and the calculated positions of the two cameras (which are offset in the z-axis) are shown on the lower right portion of the schematic.

Figure 7A:
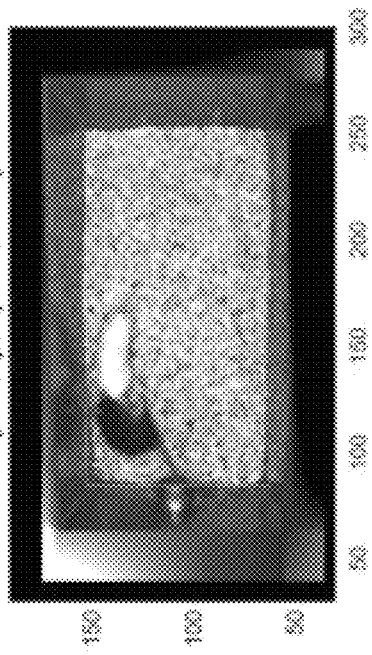
FIG. 7A shows raw depth image data acquired by a depth sensor of a behavioral classification system similar to that shown in FIGS. 3A-3D.
Figure 7B:
FIG. 7B shows registration of raw monochrome image data shown in FIG. 7C into the viewpoint of the depth sensor used to acquire the raw depth data shown in FIG. 7A.
Figure 7C:
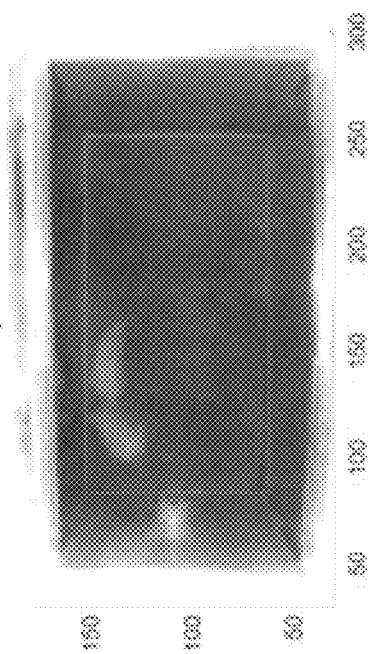
FIG. 7C shows raw monochrome image data acquired by a top view camera of a behavioral classification system similar to that shown in FIGS. 3A-3D.
Figure 7D:
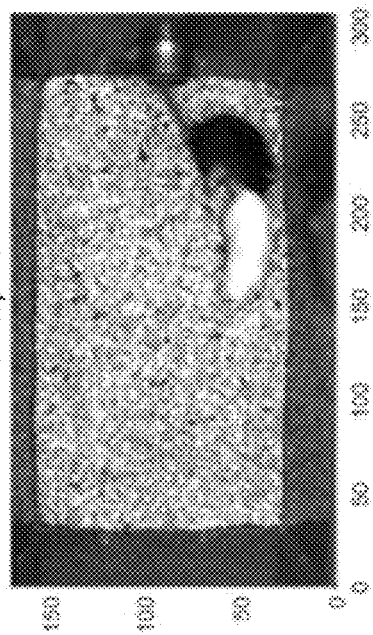
FIG. 7D shows registration of raw depth image data shown in FIG. 7A into the viewpoint of the top view camera used to acquire the monochrome image data shown in FIG. 7C.

Registration of raw depth information shown in FIG. 7A into the viewpoint of raw luminance data shown in FIG. 7C is illustrated in FIG. 7D. Registration of the raw luminance data shown in FIG. 7C into the viewpoint of the raw depth information shown in FIG. 7A is illustrated in FIG. 7B. The raw depth and luminance images are inverted due to the orientations of the respective sensors that captured the data. In other embodiments, any of a variety of calibration procedures can be utilized to obtain information used to register image data between one or more cameras and a depth sensor. In many embodiments, an off the shelf system can be utilized that automatically outputs image data in one or more color channels and registered depth maps.

Figures 8A, 8B, 8C, 8D, 8E, 8F:
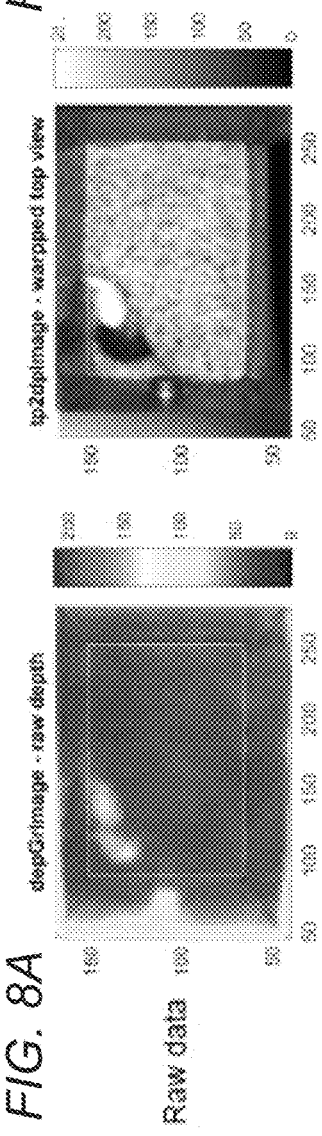
FIGS. 8A-8F conceptually illustrate background subtraction and image segmentation using reconstructed data from a top view camera and a depth sensor of a behavioral classification system similar to that shown in FIGS. 3A-3D to determine the location and identity of the two animals in accordance with an embodiment of the invention FIG. 9 conceptually illustrates a representation of pose of a rodent using an ellipse in accordance with an embodiment of the invention.

Referring again to FIG. 5, the process 500 identifies (508) the subjects and their locations within the imaged scene using image segmentation (502, 504) of both the monochrome image captured by the top view camera 304 and the depth sensor 306 and background subtraction (508). Background subtraction (508) and image segmentation (502, 504) using reconstructed data from the top view camera and depth sensor to determine the location and identity of the two animals is conceptually illustrated in FIGS. 8A-8C. FIGS. 8A and 8B show representative images of raw depth information (FIG. 8A) and luminance image data from the top view camera registered with respect to the viewpoint of the depth sensor (FIG. 8B). Segmentation of the image data is used to roughly identify a region or regions within the image data that contain the subjects. The segmented image data is illustrated in FIG. 8C. In a number of embodiments, the process 500 identifies the quadrant in which each subject is located and the background is computed by piecing together historical images of the quadrants in which no subject is located in the quadrant. The computed background can then be subtracted from the captured image data. Performing segmentation prior to background subtraction can be particularly useful in the context of home cages that have different amounts of bedding materials and thus different baseline height. As can readily be appreciated, background subtraction can be performed prior to segmentation in many processes in accordance with embodiments of the invention.

Following segmentation, background subtraction can be performed. In many embodiments, background subtraction is performed by determining a depth background for the entire cage using multiple frames of depth information and subtracting the depth background from the depth information. Subtraction of the depth background from the segmented raw image information is shown in FIG. 8D.

Referring again to FIG. 5, a second round of finer-scale location tracking (510) is performed to identify the location and pose of each of the separate subjects. In many embodiments, the identities of the animals are determined by their fur colors (black vs. white) using data from the monochrome top view camera and/or monochrome side view camera. In other embodiments, any of a variety of techniques appropriate to the requirements of the given application can be utilized for animal identification. Animals identified as the resident and the intruder segmented from image data in accordance with an embodiment of the invention are shown in FIGS. 8E and 8F. The segmented image data can be used to estimate the boundary of the animals. A boundary containing each segmented animal can then be determined (512) in each frame and used to determine (516) the orientation or pose of the animal.

Endoskeletal animals exhibit diverse and flexible postures, and their actions during any one social behavior, such as aggression, are varied. This presents a dual challenge to automated behavior classification: first, to accurately extract a representation of an animal's posture from observed data, and second, to map that representation to the correct behavior. In a number of embodiments, a low-dimensional representation of animal posture ("pose") is obtained by fitting (512) an ellipse to each animal detected in the segmented video frames. The body orientation of each animal can be determined (516) by detecting (520) its position and movement direction, as well as from features (518) detected by a previously developed machine learning algorithm.

Figure 9:
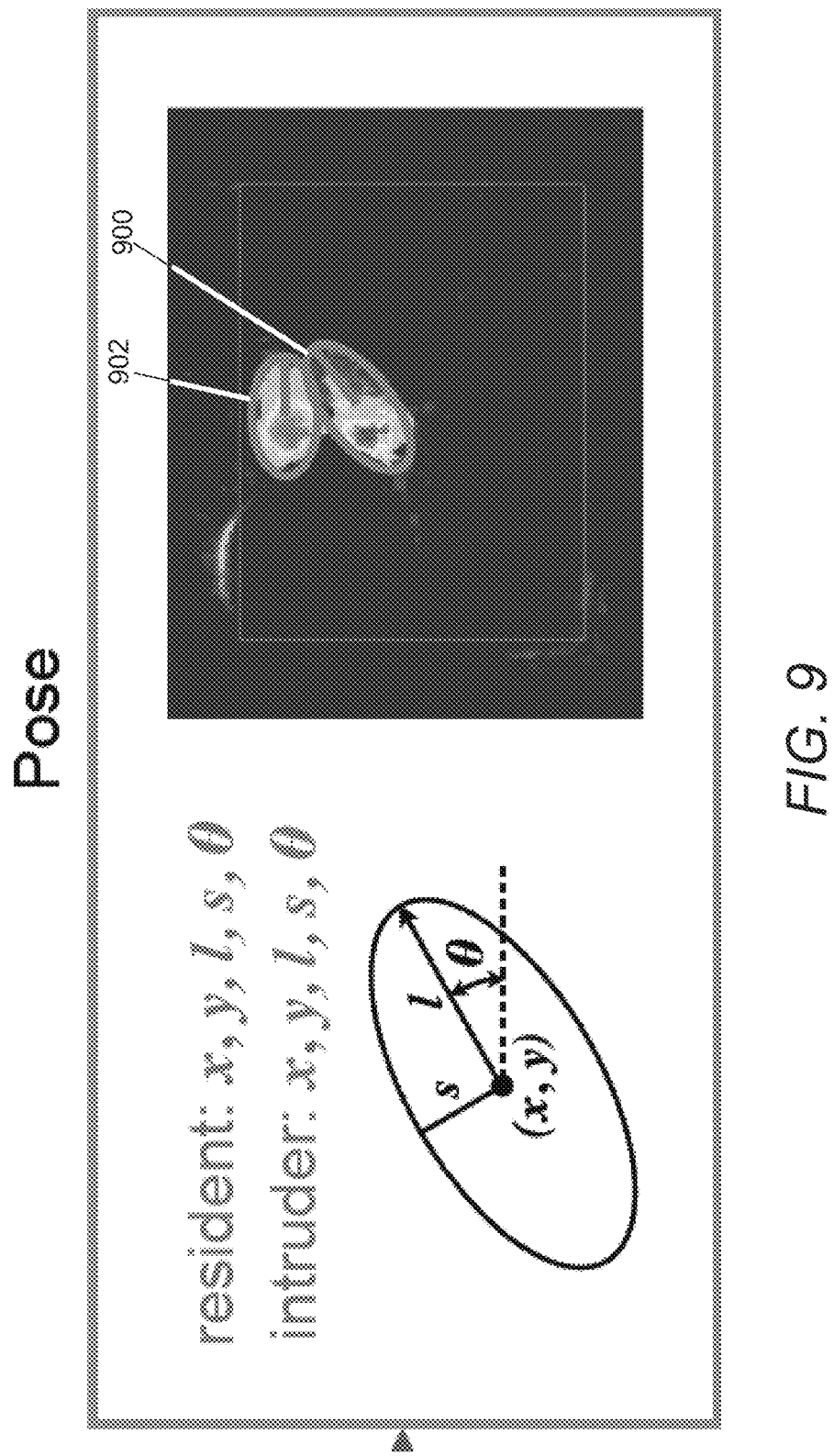
Figure 10A:
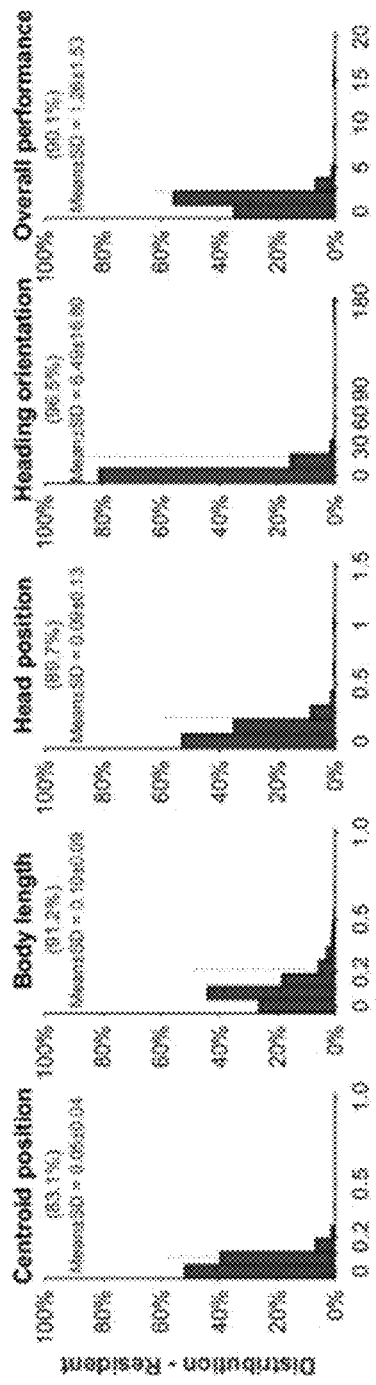
FIGS. 10A and 10B include histograms that represent the distribution of differences of individual pose parameters and overall performance between pose estimation and ground truth FIGS. 10C and 10D include histograms that provide comparisons of pose annotations between two independent human observers.
Figure 10B:
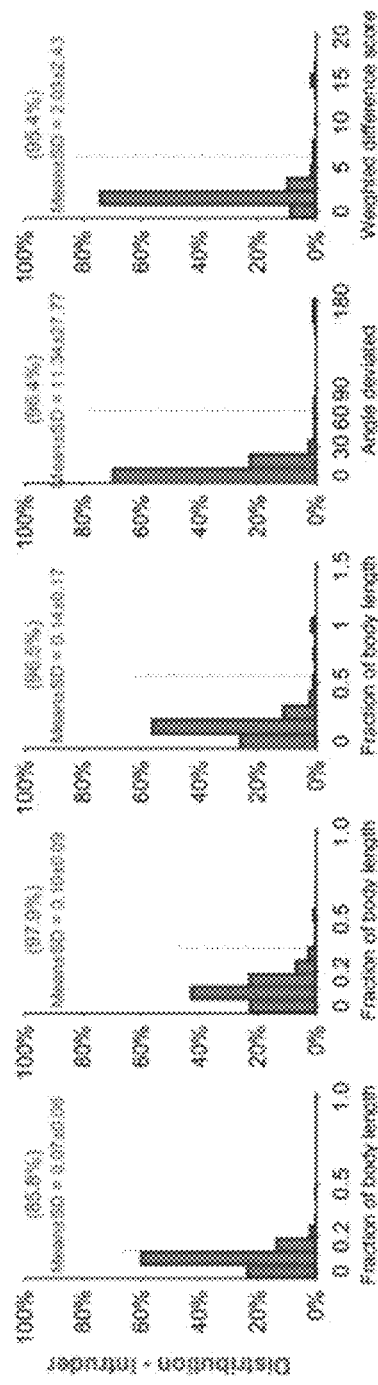

Thus, the pose of each animal can be described by a set of five parameters from the fit ellipse: centroid position (x, y), length of the major axis (l), length of the minor axis (s), and body orientation ($\theta$). Ellipses fit to a resident mouse and an intruder mouse in image data captured using the behavioral classification system shown in FIGS. 3A-3D and the parameterization of the ellipses utilizing the process 500 illustrated in FIG. 5 is shown in FIG. 9. FIG. 9 illustrates that position can be illustrated as an (x, y) or (x, y, z) Cartesian coordinate position of the center of the body of the subject, and pose (orientation) can be represented by the remaining parameterization of the ellipse. As is discussed further below, more complex models of pose can be included that utilize skeleton representations and/or other parameterizations to express information such as (but not limited to) head turning angle, curvature of the spine, curvature of the tail, and/or position of limbs. Experimental results shown in FIGS. 10A-10D show that the process 500 illustrated in FIG. 5 is able to track the position and the body orientation of the animals in a robust manner (FIGS. 10A and 10B) when compared to tracking by human annotators (FIGS. 10C and 10D). With specific regard to FIGS. 10A and 10B, each histogram represents the distribution of differences of individual pose parameters and overall performance between pose estimation and ground truth. Numbers in the parenthesis at the top of each plot represent the percentage of frames to the left of the dashed lines, which represent the 98th percentiles of the differences between two independent human observers. FIGS. 10C and 10D are comparisons of the pose annotations between two independent human observers. Dashed lines indicate $98^{th}$ percentiles of the difference for each measurement.

Figures 11A, 11B:
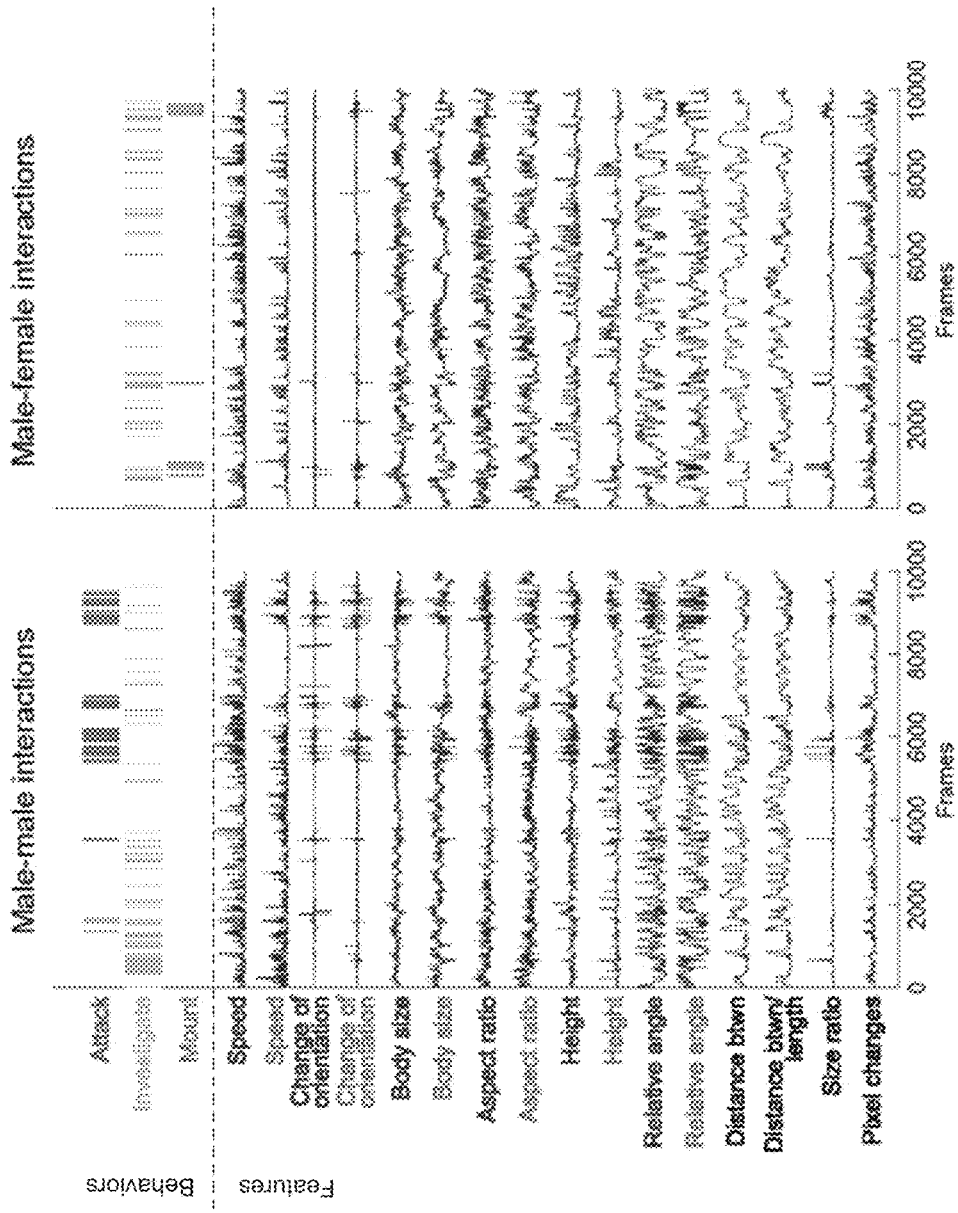
FIGS. 11A and 11B show the computation of second order features in a sequence of synchronized frames of image data.

Referring again to FIG. 5, classification is performed using the five fit ellipse parameters and an additional set of 16 second-order features describing the state of each animal in each video frame (see FIGS. 11A, and 11B), and 11 "window" features computed over multiple frames, giving 27 total features. The 27 features are described below. As noted above, any of a variety of sets of features can be utilized as appropriate to the requirements of a specific application and can be selected using techniques including (but not limited to) manually curating a set of features validated through training classifiers using the feature set and validating the trained classifier performance, and/or supervised or unsupervised analysis of the raw image data. Furthermore, the number of features that are utilized in a lower dimensional representation of tracked position and pose can be selected based upon the requirements of a specific application and may range from a small number of features to many thousands and/or millions of features as appropriate to the requirements of a given application in accordance with an embodiment of the invention. FIGS. 11A and 11B show the computation of second order features in a sequence of synchronized frames of image data. The 16 second order features are calculated from the pose and height of animals, describing the state of individual animals and their relative positions. Features that are repeated refer to a feature with respect to the resident and the same feature with respect to the intruder. The human annotations of three social behaviors are shown in the raster plot on the top to illustrate the manner in which the second order features change with different observed social behaviors.

The 27 features are provided to one or more classifiers trained to discriminate between different social behaviors. Any of a variety of classifiers can be utilized including (but not limited to) support vector machines (SVM), adaptive boosting (adaBoost), and random decision forest (TreeBagger). In many experiments, random decision forests gave the best performance in prediction accuracy and training speed. Classification performed using a random decision forest based upon the 27 extracted features was used to automatically annotate three video segments that illustrate annotated attack behavior (http://movie-usa.glencoesoftware.com/video/10.1073/pnas.1515982112/video-2), close inspection behavior (http://movie-usa.glencoesoftware.com/video/10.1073/pnas.1515982112/video-3), and mounting behavior (http://movie-usa.glencoesoftware.com/video/10.1073/pnas.1515982112/video-4). The disclosures of each of the three videos referenced above are hereby incorporated by reference herein in their entirety. While the videos demonstrate classification of social behaviors, classifiers can also be trained to identify particular non-social behaviors when subjects are not interacting. Various classifiers that can be utilized in behavioral classification systems and processes for training classifiers to perform classification of specific behaviors in accordance with a number of embodiments of the invention are discussed further below.

With specific regard to the processes described above with respect to FIG. 5, fitting ellipses to define the pose of rodents can be extremely effective in performing behavior detection. However, the use of ellipses is limited to detecting the main body trunk of the animals, and is less capable of tracking finer body parts, such as limbs, tails, whiskers, nose, eyes, ears, and mouth. Although detecting the main body trunk is sufficient to build robust classifiers for several social behaviors, use of a more complete skeleton model with finer body part resolution and tracking can provide additional information, that may allow the classification of subtler behaviors, such as self-grooming, tail-rattling, or different subtypes of attack. Furthermore, skeleton models can be utilized to extend the processes described above to any of a variety of endoskeletal animals including (but not limited to) rodents, non-human primates, and humans. Any of a variety of techniques that have been developed to fit skeletons to point clouds or meshes generated using image data in the gaming context can be adapted to fit skeletons to any of a variety of endoskeletal animals as appropriate to the requirements of specific applications in accordance with embodiments of the invention. For example, process similar to those described in Y. Yang and D. Ramanan, "Articulated pose estimation with flexible mixtures-of-parts," *Computer Vision and Pattern Recognition (CVPR)*, 2011 *IEEE Conference on*, Providence, R.I., 2011, pp. 1385-1392 can be used to estimate the pose of humans and can be adapted to perform pose estimation of non-human primates, the disclosure of which is incorporated herein by reference in its entirety. In other embodiments, any alternative skeleton model fitting and/or pose estimation process can be utilized that is appropriate to the requirements of a given application.

As can readily be appreciated, the processes described above with respect to FIG. 5 can be extended for use in a variety of contexts. A brief discussion of the 27 parameters utilized in the process 500 shown in FIG. 5 is presented below, followed by an extensive discussion of alternative processes, features, classifiers and/or classifier training techniques that can be used in behavioral classification systems in accordance with various embodiments of the invention.

Features Utilized for Mouse Social Behavior Classification

For each frame t of the recorded video, an ellipse can be fit to each animal (e.g. resident or intruder), characterized by the five parameters $\{x''(t), y''(t), l''(t), s''(t), \theta''(t)\}$, n∈{R (for the resident), I (for the intruder)}, where $(x'',y'')$ are the Cartesian coordinates of the ellipse centroid relative to the bottom left corner of the home cage, $l''$ is the length of the major axis, $s''$ is the length of the minor axis, and $\theta''$ is the body orientation in degrees (see FIG. 12A). Sixteen features can be extracted from the ten ellipse parameters (five for each animal):

Feature 1. Speed of forward motion of the resident centroid $$V(t)=\|x^R(t+4)-x^R(t-4), y^R(t+4)-y^R(t-4)\| \cdot \cos(\theta^R-\varphi^R)$$

where $\|\cdot\|$ is the Euclidean norm and $\varphi^R$ is the direction of motion of the centroids.

Feature 2. Speed of forward motion of the intruder centroid $$V(t)=\|x^I(t+4)-x^I(t-4), y^I(t+4)-y^I(t-4)\| \cdot \cos(\theta^I-\varphi^I)$$

where $\|\cdot\|$ is the Euclidean norm and $\varphi^R$ is the direction of motion of the centroids.

Feature 3. Change of the body orientation of the resident (FIG. 12B):

$$\Delta\theta^R = \mathrm{mod}(\theta^R(t) - \theta^R(t-1), 360)$$

Feature 4. Change of the body orientation of the intruder (FIG. 12C):

$$\Delta\theta^I = \mathrm{mod}(\theta^I(t) - \theta^I(t-1), 360)$$

Feature 5. Area of resident ellipse:

$$A^R(t) = \pi \frac{l^R(t)}{2} \frac{s^R(t)}{2}$$

Feature 6. Area of intruder ellipse:

$$A^I(t) = \pi \frac{l^I(t)}{2} \frac{s^I(t)}{2}$$

Feature 7. Aspect ratio between lengths of the major and minor axis of resident ellipse:

$$R^R(t) = \frac{l^R(t)}{s^R(t)}$$

Feature 8. Aspect ratio between lengths of the major and minor axis of intruder ellipse:

$$R^I(t) = \frac{l^I(t)}{s^I(t)}$$

Feature 9. Height of the highest point along the major axis of resident ellipse: given depth sensor reading $z^R(p_x, p_y, t)$ at pixel $(p_x, p_y)$ in frame t, define nine evenly spaced points along the major axis $$(s_x(i), s_y(i)) = (x^R(t), y^R(t)) + \frac{i}{5}\left(\frac{l^R(t)}{2}\cos(\theta^R(t)), \frac{l^R(t)}{2}\sin(\theta^R(t))\right) \text{ for } i \in [-4, 4]$$

Compute the average depth $Z_i^R(t)$ within a square region of width $$r = \frac{l^R(t)}{10}$$

centered at each point:

$$Z_i^R(t) = \frac{1}{2r}\sum_{p_y=s_y(i)-r}^{s_y(i)+r}\left(\frac{1}{2r}\sum_{p_x=s_x(i)-r}^{s_x(i)+r} z^R(p_x, p_y, t)\right),$$

Then take the maximum, $H^R(t) = \max(\{Z_i^R(t)\})$.

Feature 10. Height of the highest point along the major axis of intruder ellipse:

$$H^I(t) = \max(\{Z_i^I(t)\})$$

where $Z_i^I(t)$ is defined as in feature 9.

Feature 11. Relative angle between body orientation of the resident $\theta^R(t)$ and the line connecting the centroids of both animals (FIG. 12D)

$$\Phi^R(t) = \left\lfloor \mathrm{mod}\left(\theta^R(t) - \mathrm{atan2}\left(\frac{r_y(t)}{r_x(t)}\right), 360\right)\right\rfloor$$

where $\lfloor x \rfloor = \min(x, 360-x)$ and $(r_x(t), r_y(t)) = (x^R(t) - x^I(t), y^R(t) - y^I(t))$ Feature 12. Relative angle between body orientation of the intruder $\theta^I(t)$ and the line connecting the centroids of both animals (FIG. 12E):

$$\Phi^I(t) = \left\lfloor \mathrm{mod}\left(\theta^I(t) - \mathrm{atan2}\left(\frac{r_y(t)}{r_x(t)}\right) - 180, 360\right)\right\rfloor$$

where $\lfloor x \rfloor$ and $(r_x(t), r_y(t))$ are defined as in feature 11.

Feature 13. Distance between the two animals (FIG. 12F):

$$D(t) = \|x^R(t) - x^I(t), y^R(t) - y^I(t)\| - \|c^R(t)\| - \|c^I(t)\|$$

where $c^n(t) = [l^n(t)\cdot\sin(\Phi^n(t)), s^n(t)\cdot\cos(\Phi^n(t))]$, $n \in \{R, I\}$ is the length of the semi-axis of the ellipse along the line connecting the centroids of both animals, and $\Phi^n(t)$ is defined as in features 11 and 12.

Feature 14. Distance between the two animals divided by length of the semi-axis of the resident along the line connecting the two centroids:

$$R_D(t) = \frac{D(t)}{c^R(t)}$$

where $D(t)$ and $c^R(t)$ are defined as in feature 13.

Feature 15. Ratio between sizes of resident ellipses and intruder ellipses:

$$R_S(t) = \frac{A^R(t)}{A^I(t)}$$

where $A^n(t)$ is defined as in features 5 and 6.

Feature 16. Pixel changes from side-view video frames: given monochrome light intensity $f(p_x, p_y, t)$ at pixel $(p_x, p_y)$ in frame t, $$\Delta P(t) = \sum_{p_x, p_y}(f(p_x, p_y, t) - f(p_x, p_y, t-1))^2 \bigg/ \sum_{p_x, p_y}(f(p_x, p_y, t))^2.$$

Features 17-26. Smoothed features computed by averaging other extracted features over a 0.367 second window (+/-5 frames at 30 Hz, for 11 frames total). Smoothing was applied to features 1, 2, 3, 5, 6, 7, 8, 9, 10, 12, and 16 to create features 17-26, respectively.

Feature 27. Smoothed feature computed by averaging feature 16 over a 5.03 second window (+/-75 frames at 30 Hz, for 151 frames total).

While specific parameters are described above with respect to the detection of social behavior in pairs of mice, any of a variety of parameters can be utilized to create a low dimensional representation of pose and tracked motion in 3D of one or more subjects that can be utilized by a classifier to perform behavioral classification in accordance with various embodiments of the invention. Processes for training classifiers to perform behavioral detection in accordance with a number of embodiments of the invention are discussed further below.

Building Classifiers to Discriminate Between Different Behaviors

Behavioral detection classifiers in accordance with various embodiments of the invention can be trained using supervised learning or unsupervised learning. In supervised learning, classifiers are trained using data sets that have been manually annotated with the desired classifier output, to find a function that best reproduces these manual annotations. The performance of the classifier is evaluated using a testing set of ground-truth videos not used for training.

Behavioral annotation using classifiers trained using supervised learning is useful, but can have limitations. First, as the output of the classifier may simply be a binary label, it does not convey any variation in the tenor of behavior across experiments. For example, the "close investigation" behavior studied here could be further subdivided into several modes that are qualitatively or quantitatively distinct; this distinction is lost upon the classifier unless additional rounds of manual annotation and classifier training are performed to distinguish them. Second, because supervised learning requires the experimenter to define and provide training data for each new behavior to be studied, any behavior that has not been explicitly identified by the experimenter will go unnoticed. Lastly, supervised learning systems lack the ability to identify behavioral patterns that are not visually accessible to human-mediated supervised learning.

While classifiers trained using supervised learning can perform exceedingly well in many applications, issues that may be inherent to the use of supervised learning in other applications may be addressed by using classifiers that rely upon unsupervised learning. Unlike the supervised learning process, no information describing the behaviors observed within the training data set or which features to look for is provided, and the output of learning is the coordinate of each frame of video in a low-dimensional (in this case 2D) feature space. The low-dimensional feature space can then be utilized to identify clusters or islands of similar behaviors, which is the goal of unsupervised learning.

Results obtained using supervised learning and unsupervised learning to detect social behaviors exhibited by two mice using the behavioral classification system described above with respect to FIGS. 3A-3D are discussed further below.

Evaluating Performance of Behavioral Classification Using Supervised Learning

Supervised learning involves utilizing an annotated training data set to train one or more classifiers that are optimized to discriminate between the set of annotations present within the training data set. When the training data set is statistically representative of behaviors observed within real world applications, then the classifier(s) are able to robustly discriminate between the annotated behaviors when present in a real world application.

Figures 13A, 13B, 13C, 13D, 13E, 13F:
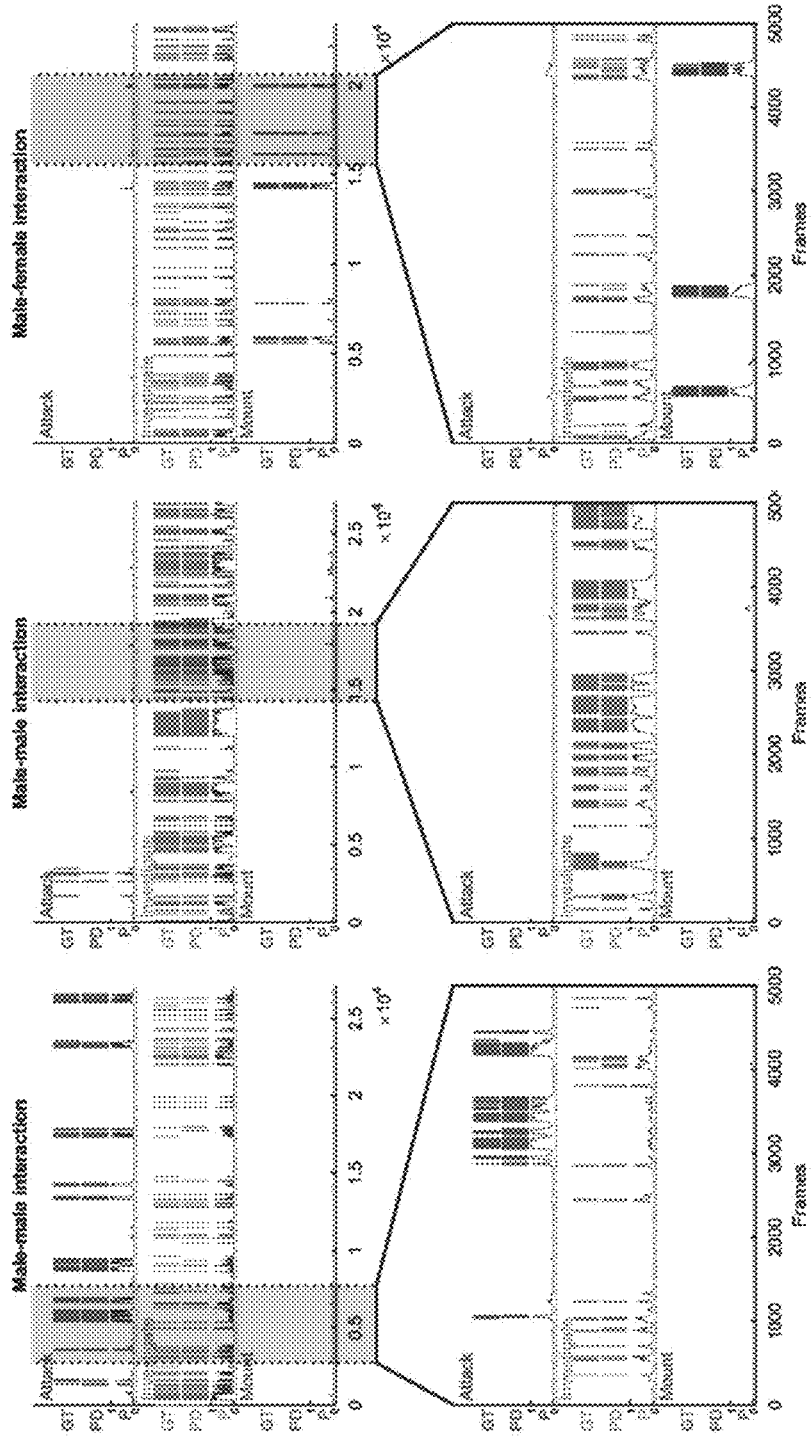
FIGS. 13A-13F show the output of the three behavior detectors for three representative videos.
Figures 13G, 13H, 13I, 13J:
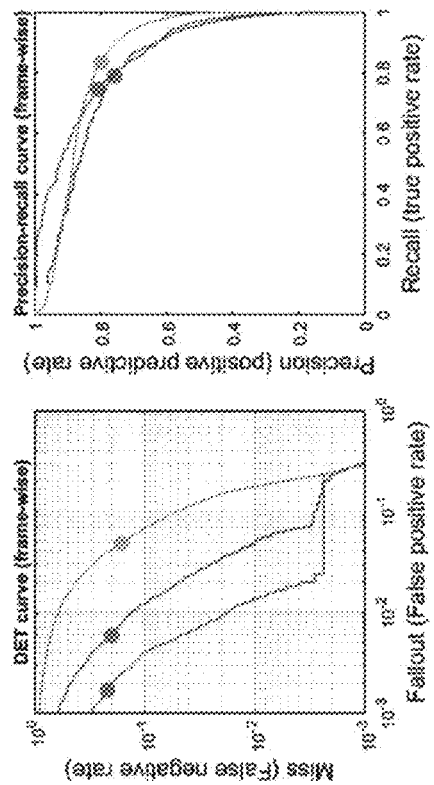
FIG. 13G charts out-of-bag error excluding in bag observations against number of grown trees for random decision forest classifiers trained in accordance with an embodiment of the invention.
FIG. 13H shows contribution of individual features to classifier performance.
FIG. 13I plots classifier performance using the detection error tradeoff (DET) curve representing the frame-wise false negative rate versus the false positive rate.
FIG. 13J plots the precision-recall curve representing the frame-wise true positive rate versus the positive predictive rate using human annotations as ground truth.

In order to evaluate the effectiveness of a random decision forests in classifying three different social behaviors (attack, mounting, and close investigation), an experiment was conducted using a training data set of six videos (recorded at 30 Hz) that contained ~150,000 frames that were manually annotated on a frame-by-frame basis. Two hundred random decision trees were generated, which was beyond where the error rate plateaued (see FIG. 13G); because individual decision trees were built independently, the process of training the decision forest is parallelizable and can be greatly sped up on a multi-core computer. The output of the three behavior detectors for three representative videos is shown in FIGS. 13A-13D (male-male interactions) and FIG. 13E-13F (male-female interactions). As seen in the expanded raster plots (FIGS. 13B, 13D, and 13F), there is a qualitatively close correspondence between ground truth and prediction bouts for attack, close investigation and mounting. The contribution of individual features to classifier performance is shown in FIG. 13H.

Figure 13K:
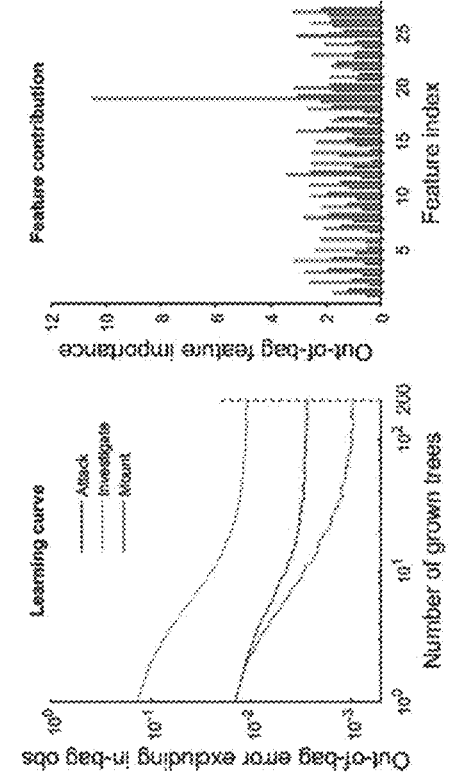
FIG. 13K shows frame-wise precision, recall, fallout, and accuracy rates at a classification threshold chosen to optimize frame-wise precision and recall.

To measure the accuracy of these behavior classifiers in replicating human annotations, a set of 14 videos was manually labeled (not including the videos used to train the classifier) that contained ~350,000 frames from a variety of experimental conditions and classifier error was measured on a frame-by-frame basis. Classifier performance using the detection error tradeoff (DET) curve representing the frame-wise false negative rate versus the false positive rate is plotted in FIG. 13I and the precision-recall curve representing the frame-wise true positive rate versus the positive predictive rate is plotted in FIG. 13J, using the human annotations as ground truth. These measurements illustrated the tradeoff between the true positive rate versus the positive predictive value at different classification thresholds from 0 to 1. A classification threshold was chosen that optimized the frame-wise precision and recall; the frame-wise precision, recall, fallout, and accuracy rates at the classification threshold are shown in FIG. 13K. The classifiers showed an overall prediction accuracy of 99% for attack, 99% for mounting, and 92% for close-investigation. Lastly, the precision and recall rates at the level of individual behavioral episodes ("bouts") were measured, as were periods in which all frames were labeled for a given behavior. A high level of bout-wise precision and recall were observed across a range of minimum bout durations (see FIG. 13K). Accordingly, the experimental data demonstrated that supervised learning can be utilized to train classifiers to robustly detect behaviors based upon tracked motion of subjects in 3D. As can readily be appreciated, similar results can be obtained using behavioral classification systems that rely upon any of a variety of classifiers and that perform classification of behaviors of one or more subjects generally.

Evaluating Performance of Behavioral Classification Using Unsupervised Learning

Unsupervised classifiers can provide the power to detect unique behavioral "maps," which reflect sensitive changes in an animal's genetic make-up or environmental condition. This ability in turn can open up a host of biologically relevant and stimulating questions that can be answered for the first time. For example, do animals fight differently when they are stressed? How are mating tactics altered by female receptivity? Is close investigation divergent across species and/or dependent on early environmental factors such as pre-pubescent socialization? Do strains of mice with varying levels of aggressiveness exhibit purely quantitative differences, or are there qualitative differences in the pattern of attack as well? Such questions are vital towards our understanding of animal (and eventually human) behavior, and its control by neural circuit activity. Moreover, use of an unsupervised learning layer in behavioral classification systems in accordance with a number of embodiments of the invention allows, in principle, for the detection of behavioral repertoires that could have been overlooked or missed by a human observer. For example, differences in close investigation clusters may reveal subtle differences in animals' experiential past or genetic conditions. Perhaps alpha males have a unique fighting cluster that is unobserved in any other male. What would such a cluster mean? How could it be further tested and investigated? Hence, use of unsupervised learning in behavioral classification systems in accordance with many embodiments of the invention are not only capable of answering questions, but also of providing tools from which new, exciting questions in biology may be generated.

The complimentary use of supervised and unsupervised learning methods was demonstrated by testing a recently developed unsupervised learning technique on the same set of ~500,000 frames analyzed with the supervised classifiers described above. 3D tracking is initially performed to estimate the pose of each animal, and extract a set of 27 features. Spectrograms of the extracted features are generated using the Morlet continuous wavelet transform, replacing the features from each frame with a spectral representation of how each feature varied on multiple timescales. This representation has been found to be useful in distinguishing between behaviors, many of which are best identified by the dynamics and statistics of animal movement rather than their static positions. A nonlinear dimensionality reduction algorithm can be applied to the spectrograms such as (but not limited to) t-distributed stochastic neighbor embedding (t-SNE), to embed the high-dimensional feature data into a two-dimensional visualizable space. Like other forms of nearest-neighbor embedding, t-SNE penalizes embedding-induced distortions of the high-dimensional data with a cost function that falls off sharply with the dissimilarity between points; as a result, frames with very similar representations in feature space are mapped to nearby coordinates in the 2D embedding space. The embedded data can be visualized as a smoothed 2D histogram, and divided into distinct clusters for analysis by applying the watershed algorithm. See for example the histogram shown in FIG. 14A).

To study the representation of behaviors in the 2D embedding space, the ~500,000 embedded frames were manually annotated as corresponding to aggression, mounting, or close inspection behavior. As can be seen in FIGS. 14B-14D, the aggression (FIG. 14B) and mounting (FIG. 14C) frames are restricted into discrete clusters, while close investigation frames (FIG. 14D) were distributed in several clusters and appeared to be more heterogeneous, though these clusters are still somewhat separated from clusters corresponding to other behaviors. Since each cluster here was defined by machine as opposed to human, it is intriguing to see that different social behaviors are well isolated in a small number of clusters, showing the power of unsupervised learning. As can be seen in FIG. 14E, frames that do not belong to any of the three labeled behaviors were also distributed in many clusters, and can be further examined to yield additional behaviors of interest.

As with classifiers trained using supervised learning, experiments were performed to determine whether unsupervised learning could be used to compare the behavioral repertoire of animals under different experimental conditions (FIGS. 14F-14H). Behaviors that occurred during male-female vs. male-male interactions were compared (FIGS. 14F-14G), resulting in a finding that the embedded frames from two conditions were distributed in very different sets of clusters. In particular, a distinct cluster corresponding to mounting behaviors was visible in male-female encounters, and absent in male-male encounters (FIGS. 14F and 14G). The distribution of close investigation frames in embedding space was also notably different for male-male encounters vs. male-female encounters, suggesting that differences might exist between male-directed vs. female-directed close inspection.

Detection of social behavior of two strains of mice, C57BL/6N and NZB/B1NJ, using classifiers trained by unsupervised learning during male-male interactions (FIGS. 14G and 14H) were also studied, resulting in the finding that the embedded frames from the two strains were distributed in very different sets of clusters. Embedding produced a distinct cluster corresponding to attack behavior in NZB/B1NJ (FIG. 14H), which was largely absent in C57BL/6N. To test whether strain and intruder sex effects on embedding were significant, the distribution of frames in the 2D embedding space was examined. All embedded movies were divided into two-minute clips, and counts were generated of the number of frames embedded within each of 31 2D regions delineated by running the watershed algorithm on the entire dataset. A multivariate ANOVA test (MANOVA) was performed on the cluster membership counts of all clips, to test whether the separation between class means was significant compared to the variance in embeddings within a class. The MANOVA test showed with high significance that the separation of class means was significant ($p=0.31e-9$ that class means could be described with less than N−1 canonical dimensions—see FIGS. 14I-14J). Together, these data show how the behavioral classification processes described herein can be used in conjunction with unsupervised learning as a useful tool for directing and clarifying investigation of social behaviors, and detecting differences in behavioral repertoire under different experimental conditions in a user-unbiased manner.

Detecting Genetic Influences on Social Behaviors

The experiments conducted using unsupervised learning described above explored the relationship between genotype and specific behavioral phenotypes. Additional experiments were conducted using classifiers trained via supervised learning to track several biologically relevant behaviors under differing experimental conditions to examine how genetic backgrounds (in this case, different inbred lines of mice) influence social behaviors. Annotations of resident male behavior during interactions with either a male or a female intruder ($I_m$ vs. $I_f$, respectively) were performed using classifiers trained via supervised learning. The percentage of time resident males spent engaging in attack, mounting, and close investigation of conspecifics was observed (FIGS. 15A-15C; note that this parameter is not directly comparable across behaviors, because the average bout length for each behavior may be different). Measurements were also made with respect to the total numbers of bouts during recording (FIGS. 15D-15F), the latency to the first bout of behavior for each resident male (FIGS. 15G-15I), and the distribution of bout lengths for each behavior (FIGS. 15J-15R). We observed that for our standard strain C57BL/6N, male residents ($R_{C57N}$) exhibited more close investigation bouts with longer duration toward males (FIG. 15N; $I_m$) than that toward female (FIG. 15K; $I_f$) intruders ($p<0.001$), although the total numbers of bouts was comparable between the two conditions (FIG. 15E). The classifier predictions showed no significant differences from the ground truth in the measured percentage of time spent engaging in each behavior, nor in the bout length distribution of each behavior (FIGS. 15K, 15N, and 15Q; yellow vs. gray bars) (~350,000 frames total), suggesting that the same classifiers work robustly in both male-male and male-female interactions.

To examine how genetic backgrounds influence social behaviors, a comparison was performed between two strains of resident male mice, C57BL/6N and NZB/B1NJ. NZB/B1NJ mice have been observed to be more aggressive than C57BL/6N mice. Consistently, we found that NZB/B1NJ resident males spent more time attacking BALB/c intruder males, and significantly less time engaging in close investigation, than did C57BL/6N resident males (FIGS. 15A and 15B; $R_{NZB}$) (p<0.05). This likely reflects a more rapid transition from close investigation to attack, since the average latency to attack was much shorter for NZB/B1NJ than for C57BL/6N males (FIG. 15G). Interestingly, NZB/B1NJ animals exhibited both a higher number of attack bouts (FIG. 15D) (p<0.05) and longer average attack durations compared to C57BL/6N animals (FIGS. 15M and 15P) (p<0.05). These data illustrate the ability of behavioral classification systems in accordance with various embodiments of the invention to reveal differences between the manner in which subjects having different genotypes (e.g. NZB/B1NJ and C57BL/6N males) socially interacted. In all measurements, the classifier prediction showed no significant differences from the ground truth, suggesting that the same classifiers work robustly with subjects having distinct genotypes that exhibit very different social behaviors. The use of behavioral classification systems in accordance with various embodiments of the invention to study the relationships between genotypes and behavioral phenotypes is discussed further below.

Detection of Social Deficits in a Mouse Autism Model

Figure 16A:
FIGS. 16A-16C chart observations of social investigation performed by BTBR animals in comparison to C57BL/6N controls.
Figure 16B:
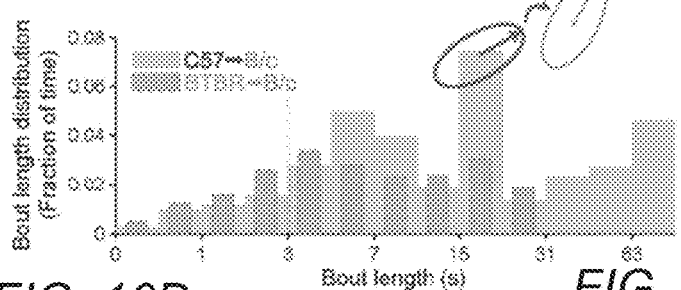
Figure 16C:
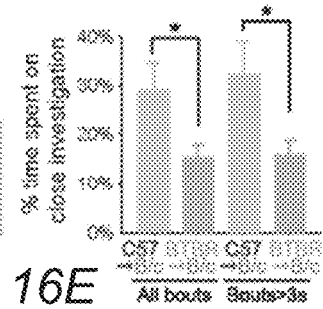

Behavioral classification systems in accordance with a number of embodiments of the invention can be utilized to detect social deficits in mouse models of autism. BTBR T+tf/J (BTBR) mice are an inbred mouse strain that has been shown (using manual annotation) to display autism-like behavioral phenotypes, such as reduced social interactions, compared to C57BL/6N animals. In one series of experiments utilizing a behavioral classification system to perform automatic behavior detection, social interactions between BTBR mice (or C57BL/6N control mice) and a "target" animal of the Balb/c strain, in an unfamiliar, neutral cage were observed. Significantly less social investigation was observed as being performed by BTBR animals in comparison to C57BL/6N controls (FIG. 16A-16C), consistent with previous reports. In particular, the BTBR animals displayed shorter bouts of (FIG. 16B), and reduced total time engaged in (FIG. 16C), social investigation.

Figure 17B:
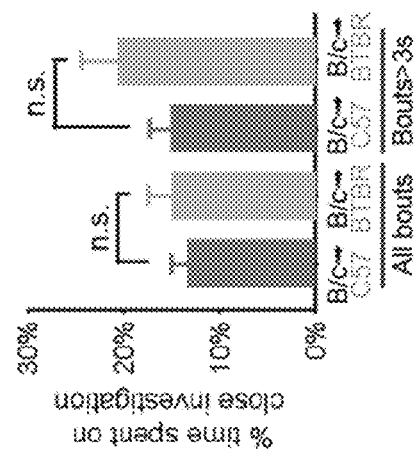
FIGS. 17A and 17B chart observations of social investigation performed by Balb/c animals in comparison to C57BL/6N controls.
Figure 17D:
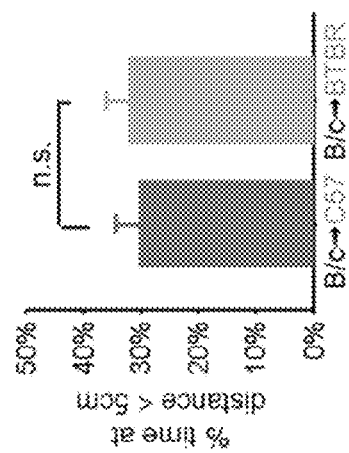
FIGS. 17C and 17D chart measurements of "head-body" distance in Balb/c mice animals paired with BTBR vs. C57BL/6N mice.
Figure 17A:
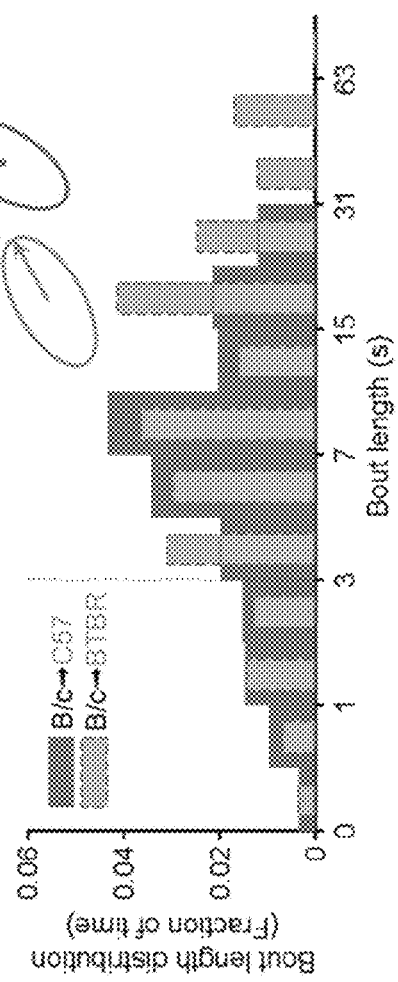

To determine whether this reduction of social investigation reflects less investigation of the Balb/c mouse by the BTBR mouse (in comparison to the C57BL/6N controls), or vice-versa, measurements of the social investigation behavior performed by the Balb/c mouse were obtained. Balb/c animals did not exhibit reduced social interactions with the BTBR mice in comparison to C57BL/6N controls (FIG. 17A-17B). This suggests that the reduction of social investigation observed in BTBR animals is indeed due to less investigation of the Balb/c mouse by the BTBR mouse.

Figure 16D:
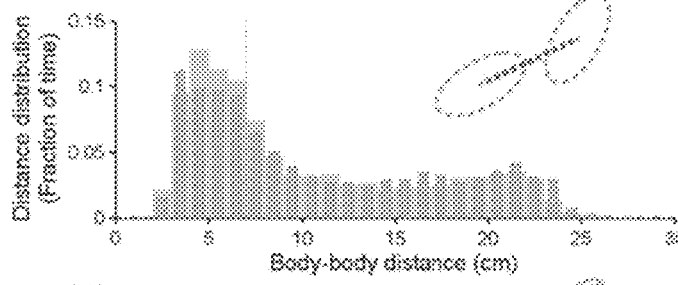
FIGS. 16D and 16E chart observations of body-body distances in BTBR animals paired with Balb/c mice.
Figure 16E:
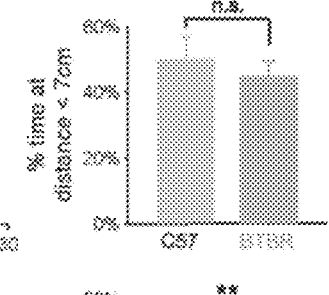
Figure 16F:
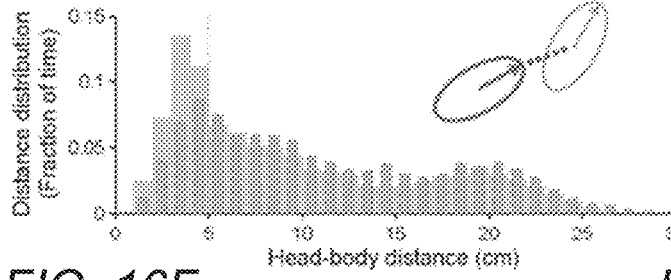
FIGS. 16F and 16G chart measurements of "head-body" distance in BTBR animals paired with Balb/c mice.
Figure 16G:
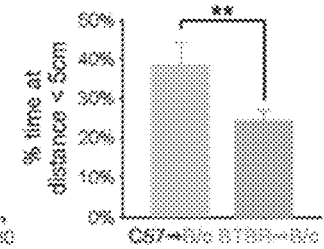
Figure 17C:
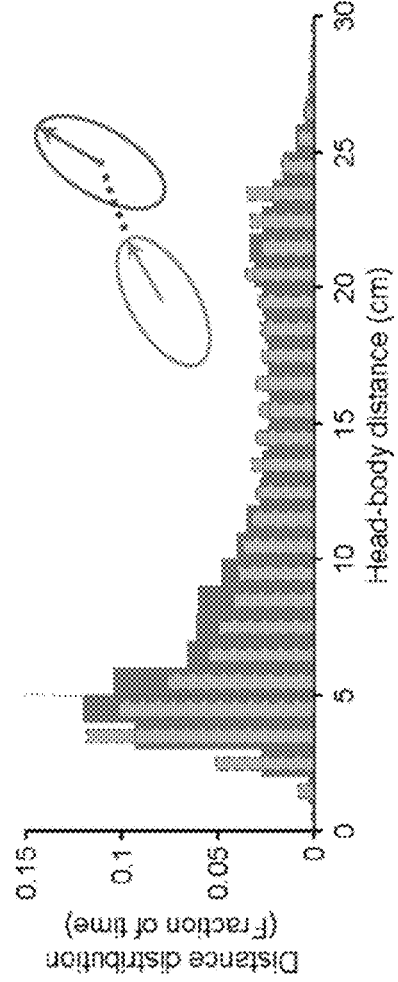

Lastly, an investigation was conducted with respect to the question of whether pose estimation and supervised behavioral classifications offered additional information beyond tracking animal location alone. Initially, "body-body" distance was measured—the distance between centroid locations of two interacting animals (illustrated in the schematic in FIG. 16D)—a measurement that only used the output from tracking animal location alone but not from pose estimation or behavioral classifiers. A trend involving decreased time spent at short body-body distances (<6 cm) in BTBR animals was observed (FIGS. 16D and 16E), but this effect was not statistically significant. When measurements were made of "head-body" distance—the distance between the front end of the subject and the centroid of the other animal (illustrated in the schematic in FIG. 16F)—a measurement that used output from both tracking and pose estimation, but not from supervised behavioral classifications—a statistically significant reduction in time spent at short (<4 cm) head-body distances in BTBR animals paired with Balb/c mice was observed (FIGS. 16F and 16G), compared to that in C57BL/6N animals paired with Balb/c. This difference did not reflect reduced investigation of BTBR animals by Balb/c mice, as the latter did not show a significant difference in time spent at short head-body distances towards BTBR vs. C57BL/6N mice (FIGS. 17C and 17D). Rather, the difference reflects reduced close investigation of Balb/c mice by BTBR mice in comparison to C57BL/6N controls. These data together suggest that the behavioral classification system was able to detect social behavioral deficits in BTBR mice, a mouse model of autism, and that compared to animal location tracking alone, pose estimation and supervised behavioral classification provide additional useful information in detecting behavioral and phenotypic differences.

As can readily be appreciated the above results demonstrate that behavioral classification systems in accordance with a number of embodiments of the invention can be utilized to detect specific behavioral patterns indicative a behavioral phenotype. Furthermore, when a strong relationship exists between one or more observed behavioral phenotypes and a specific genotype or genetic background, behavioral classification systems in accordance with many embodiments of the invention can use the detection of the observed phenotypes to predict the existence of, or the likelihood of, a particular genotype. The ability to detect behavior can also be utilized to evaluate the effectiveness of pharmaceuticals in treating a behavioral phenotype and/or in the detection of adverse side effects. The use of behavioral classification systems to detect behavioral phenotypes and in the (high-throughput) study of pharmaceuticals is discussed further below.

Classification of Higher Level Behaviors

Automated annotation of image data using detected behaviors creates an opportunity to use patterns of identified behaviors to identify higher level behaviors (e.g. goals) and/or complex behavioral phenotypes. Behavioral classification systems in accordance with a number of embodiments can utilize sequences of behavioral data to train classifiers to detect complex patterns of behavior, goals, and/or states of mind when monitoring humans and potentially some species of animal. In a number of embodiments, sequences of detected behaviors are utilized to train models such as (but not limited to) Hidden Markov Models, and/or neural networks that can be utilized to perform behavioral pattern detection. As can readily be appreciated, the specific classifiers utilized to detect patterns of behavior will typically depend upon the requirements of a particular classification task.

High-Throughput Behavioral Classifiers

A major advantage of behavioral classification systems in accordance with various embodiments of the invention is increased throughput, increased consistency and accuracy, and decreased labor-intensiveness. Typically, it takes about six hours of manual labor to score each hour of video, on a frame-by-frame basis at 30 Hz, particularly if multiple behaviors are being analyzed. A typical study using social behavior as a quantitative readout may require analyzing dozens or scores of hours of video recordings. Behavioral classification systems in accordance with many embodiments of the invention can reduce the time requirements for analysis to an initial commitment of several hours to manually generate a training set of annotations and a few minutes to train the classifier, after which large numbers of additional videos can be scored in a matter of minutes. This not only eliminates major bottlenecks in throughput, but can improve the statistical power of behavioral studies by enabling larger sample sizes; this is often a problem for behavioral assays which typically exhibit high variance. Behavioral classification systems in accordance with several embodiments of the invention also open up the possibility of using behavioral assays as a primary, high-throughput screen for drugs or gene variants affecting mouse models (or other animal models) of social interaction disorders, such as autism. In addition to this time- and labor-saving advantage, while human observers may fail to detect behavioral events due to fatigue or flagging attention, miss events that are too quick or too slow, or exhibit inconsistencies between different observers in manually scoring the same videos, supervised behavior classifiers can apply consistent, objective criteria to the entire set of videos, avoiding potential subjective or irreproducible annotations. In addition, unsupervised training of classifiers can reveal important behaviors that are not otherwise readily observable to a human observer.

As noted above with respect to the discussion of FIG. 1, high-throughput behavioral classification can involve the collection of vast amounts of image data. In several embodiments, the image data is captured locally on hard drives and processed remotely. The hard drives may be physically transported to the computing systems that perform the behavioral classification, or the data may be transferred via a network. In several embodiments, each imaging system is coupled to a computing system that processes the image data in real time or near real time and forward the results of analysis to a computing system that aggregates data across the high-throughput behavioral classifier. In certain embodiments, the imaging system incorporates an FPGA that performs 3D tracking and/or behavioral classification and streams data to a computer system. Specific implementations of high-throughput behavioral classification systems are typically determined by the requirements of a given application. As discussed further below, the study and screening of pharmaceuticals is a particularly important application of high-throughput behavioral classification.

Pharmaceutical Screening

Behavioral classification systems in accordance with many embodiments of the invention can be utilized to observe modifications in behavior that result from administration of a pharmaceutical. In many embodiments, a behavioral baseline is established and deviations from the behavioral baseline are observed following administration of a pharmaceutical. In several embodiments, the pharmaceutical is administered to subjects that possess a specific behavioral phenotype associated with a behavioral disorder (e.g., due to a deliberate genetic and/or environmental manipulation) and the effectiveness of the pharmaceutical in treating the behavioral phenotype is measured. In a number of embodiments, the pharmaceutical is administered to a population and the behavior of the population is monitored to observe variance in behavior that may be associated with an adverse drug reaction. In other embodiments, large numbers of compounds ("libraries") of previously unknown behavioral effects are tested on large numbers of animals to identify those compounds that may ameliorate particular behavioral phenoptypes or "symptoms". In many embodiments, the behavioral classification system observes the behavior of an individual. In certain embodiments, the behavioral classification system observes social behavior of a subject to which the pharmaceutical has been administered.

While specific uses of behavioral classification systems in analyzing the effect of administering pharmaceuticals to a subject are described above, the manner in which a behavioral classification system in accordance with an embodiment of the invention can be utilized in the study of pharmaceuticals is typically determined by the requirements of a specific study.

Differentiating Between Social Behaviors Based Upon Observations of a Single Subject Much of the discussion of detection of social behavior described above involves the observation of two or more subjects and observing interactions between the subjects. As can readily be appreciated, a considerable benefit exists in being able to classify social behavior when observing only one subject engaging in the social behavior. In a number of embodiments of the invention, processes similar to those described above are utilized to generate low dimensional representations of tracked pose and motion of a subject that are provided to a classifier for the purposes of behavioral classification. In several embodiments, image data can be captured from a viewpoint approximating the viewpoint of an individual with whom the subject is interacting and distance between the subject and the imaging system utilized as a proxy for distance between the subject and the individual with whom the individual is interacting.

In many embodiments, image data captured using body cameras and/or vehicle mounted cameras can be utilized to provide alerts (in real time) when specific types of behavior are observed. In several embodiments, alerts can be utilized to assist in the provision of behavioral therapy by detecting social behavior in a subject and alerting the patient to behavior of the subject using any of a variety of output devices including (but not limited to) a heads up display, an audible alert generated by a speaker, and/or a vibration generated by a vibrotactile feedback mechanism. In other embodiments, a first responder wearing a body camera is alerted by an output device that a subject visible within the field of view of the imaging system may be exhibiting aggressive behavior and/or intoxicated behavior. In this way, the behavioral classification system can augment the decision making process of the first responder in engaging the subject. Behavioral classification systems in accordance with many embodiments of the invention could also be utilized in a similar way by animal handlers, and/or by individuals in the wilderness that may encounter wild animals, or in urban settings that may encounter potentially threatening pets (e.g., dogs).

As can readily be appreciated, behavioral classification systems that can detect social behavior of a single subject can be utilized in any of a variety of applications. One such application is the annotation of measurement data captured simultaneously with the image data used to perform the behavioral classification. The annotation of measurement data using automatically detected behaviors in accordance with various embodiments of the invention is discussed further below.

Annotating Measurement Data Based Upon Automatically Detected Behaviors

Many of the behavioral classification systems described above synchronize image data captured by one or more cameras and one or more depth sensors to perform automated tracking and quantification of specific behaviors. In several embodiments, the detected behavior data generated by a behavioral classification system can be synchronized with other measurements performed during capture of the image data. For example, behavioral classification systems can detect behaviors with a time resolution (e.g. 30 Hz) commensurate with that of functional imaging of neuronal activity in the brains of freely moving animals, using fluorescent calcium or voltage sensors, or using electrodes to measure current or voltage changes in nerve cells. Accordingly, behavioral classification systems in accordance with various embodiments of the invention can synchronize detected behavior data with measurements of neuronal activity enabling correlative and causal analysis of the brain mechanisms that underlie complex social behaviors. Synchronization of behavioral measurement data and detected behavior data is simply one example of a wide variety of measurements that can be usefully annotated with detected behavior data in accordance with differing embodiments of the invention. As can readily be appreciated, a behavioral classification system in accordance with an embodiment of the invention can readily synchronize detected behavior data with any time stamped measurement (e.g., of physiological, psychological or molecular parameters). Furthermore, time stamped synchronized detected behavior data can be provided to any number of different computing system for use in conjunction with other measurements.

Although the present invention has been described in certain specific aspects, many additional modifications and variations would be apparent to those skilled in the art. It is therefore to be understood that the present invention may be practiced otherwise than specifically described, including various changes in the implementation such as the use of classifiers other than those described herein, without departing from the scope and spirit of the present invention. Thus, embodiments of the present invention should be considered in all respects as illustrative and not restrictive.

What is claimed is:

1. A behavioral classification system, comprising:
   a microprocessor; and
   memory containing a classification application;
   wherein the classification application directs the microprocessor to:
      identify at least a primary subject interacting with a secondary subject within a sequence of frames of image data comprising depth information;
      determine poses for at least the primary subject and the secondary subject within a plurality of frames from the sequence of frames of image data;
      extract a set of parameters describing the poses and movement of at least the primary and secondary subjects from the plurality of frames from the sequence of frames of image data; and
      detect a social behavior performed by at least the primary subject and involving at least the secondary subject, wherein the primary subject occludes at least a portion of the secondary subject, using a classifier trained to discriminate between a plurality of social behaviors based upon the set of parameters describing poses and movement of a plurality of subjects extracted from a plurality of frames of image data comprising depth information.

2. The behavioral classification system of claim 1, wherein the classifier is trained to discriminate between a plurality of social behaviors using a training data set comprising a plurality of sequences of frames of image data comprising depth information.

3. The behavioral classification system of claim 2, wherein:
   each sequence of frames of image data comprising depth information in the training data set is annotated using one of a predetermined set of a plurality of social behaviors; and
   the classifier is trained to discriminate between behaviors within the predetermined set of a plurality of social behaviors.

4. The behavioral classification system of claim 2, wherein:
   the training of the classifier using the training data set automatically generates a set of a plurality of social behaviors observed in the training data set; and
   the classifier is trained to discriminate between behaviors within the automatically generated set of a plurality of social behaviors observed in the training data set.

5. The behavioral classification system of claim 1, wherein the classification application further directs the microprocessor to detect occurrence of modified social behavior in at least the primary subject resulting from administration of a pharmaceutical.

6. The behavioral classification system of claim 1, wherein the classification application further directs the microprocessor to detect a behavioral phenotype associated with a genotype of the primary subject based upon detection of a pattern of social behaviors including the detected social behavior by a set of subjects including at least the primary subject that share the same genotype.

7. The behavioral classification system of claim 1, wherein the primary and secondary subjects are rodents.

8. The behavioral classification system of claim 7, wherein the plurality of behaviors comprise a plurality of behaviors selected from the group consisting of: attack, close inspection, mounting, chasing, social grooming, maternal behavior, paternal behavior, female receptivity, and social feeding.

9. The behavioral classification system of claim 7, wherein the classification application further directs the microprocessor to detect occurrence of modified social behavior in at least the primary subject resulting from administration of a pharmaceutical.

10. The behavioral classification system of claim 7, wherein the classification application further directs the microprocessor to detect a behavioral phenotype associated with a genotype of the primary subject based upon detection of a pattern of social behaviors including the detected social behavior by a set of subjects including at least the primary subject that share the same genotype.

11. The behavioral classification system of claim 1, wherein the primary and secondary subjects are non-human primates.

12. The behavioral classification system of claim 11, wherein the classification application further directs the microprocessor to detect occurrence of modified social behavior in at least the primary subject resulting from administration of a pharmaceutical.

13. The behavioral classification system of claim 11, wherein the classification application further directs the microprocessor to detect a behavioral phenotype associated with a genotype of the primary subject based upon detection of a pattern of social behaviors including the detected social behavior by a set of subjects including at least the primary subject that share the same genotype.

14. The behavioral classification system of claim 1, wherein the classification application directs the microprocessor to identify at least a primary subject interacting with a secondary subject within a sequence of frames of image data comprising depth information by:

performing background subtraction using a plurality of frames of image data; and performing segmentation of at least a primary subject and a secondary subject.

15. The behavioral classification system of claim 14, wherein the classification application further directs the microprocessor to identify at least a primary subject interacting with a secondary subject within a sequence of frames of image data comprising depth information based upon characteristic markings of primary and second subjects visible within frames of image data comprising video data in at least one color channel.

16. The behavioral classification system of claim 1, wherein the classifier is selected from the group consisting of a support vector machine, adaptive boosting, and a random decision forest.

17. The behavioral classification system of claim 1, wherein the image data further comprises video data in at least one color channel.

18. The behavioral classification system of claim 17, further comprising:
 a 3D imaging system;
 wherein the classification application further directs the microprocessor to:
  control the 3D imaging system to acquire the sequence of frames of image data comprising depth information and video image data in at least one color channel; and
  store the sequence of frames of image data comprising depth information in memory.

19. The behavioral classification system of claim 18, wherein the 3D imaging system is selected from the group consisting of:
 a time of flight depth sensor and at least one camera;
 a structured light depth sensor and at least one camera;
 a LIDAR depth sensor and at least one camera;
 a SONAR depth sensor and at least one camera;
 a plurality of cameras in a multiview stereo configuration; and
 a plurality of cameras in multiview stereo configuration and an illumination source that projects texture.

20. The behavioral classification system of claim 19, wherein the 3D imaging system further comprises an additional camera.

21. The behavioral classification system of claim 19, wherein the camera is selected from the group consisting of a monochrome camera, a Bayer camera, and a near-IR camera.

22. The behavioral classification system of claim 1, wherein the classification application further directs the microprocessor to:
 extract a set of parameters describing the poses and movement of at least the primary and secondary subjects from the plurality of frames from the sequence of frames of image data and from additional sensor data; and
 the classifier is trained to discriminate between a plurality of social behaviors based upon the set of parameters describing poses and movement of a plurality of subjects extracted from a plurality of frames of image data comprising depth information and additional sensor data.

23. The behavioral classification system of claim 22, wherein the additional sensor data comprises at least one piece of sensor data selected from the group consisting of:
 audio data;
 motion detection data;
 pressure sensor data;
 temperature data; and
 ambient lighting data.

24. The behavioral classification system of claim 1, wherein the classification application further directs the microprocessor to associate the detected social behavior performed by at least the primary subject with measurement data acquired during the time period in which the detected social behavior was observed in the sequence of frames of image data.

25. The behavioral classification system of claim 24, wherein the measurement data measures a characteristic of the primary subject selected from the group consisting a physiological characteristic, a psychological characteristic, and a molecular characteristic.

26. The behavioral classification system of claim 24, wherein the measurement data measures neuronal activity.

27. The behavioral classification system of claim 1, wherein the classification application further directs the microprocessor to:
 detect a sequence of a plurality of social behaviors performed by at least the primary subject and involving at least the second subject using the classifier, where the detected behaviors are actions; and
 identify an activity state of at least the primary subject from amongst a plurality of activity states based upon the detected sequence of a plurality of social behaviors using a classifier trained to discriminate between a plurality activity states based upon a detected sequence of at least one social behavior performed by a subject.

28. The behavioral classification system of claim 1, wherein the detected social behavior is selected from the group consisting of an action and an activity.

29. The behavioral classification system of claim 1, wherein the classification application directs the microprocessor to detect non-social behaviors performed by at least the primary subject.

30. The behavioral classification system of claim 29, wherein the detected non-social behaviors are selected from the group consisting of: self-grooming, scratching, digging, circling, walking, running, nesting, freezing, flattening, jumping, thigmotaxis, rearing, risk-assessment (stretched-attend posture), climbing, eating, drinking, burying, and sleeping.

31. A behavioral classification system, comprising:
 a plurality of 3D imaging systems; and
 a behavioral classification computer system comprising at least one memory and at least one microprocessor directed by at least a classification application stored in the at least one memory to:
  control the plurality of 3D imaging systems to each acquire a sequence of frames of image data comprising depth information;
  store at least a portion of each of the sequences of frames of image data comprising depth information in the at least one memory; and
  for each of the sequences of frames of image data:
   identify at least a primary subject interacting with a secondary subject within a given sequence of frames of image data comprising depth information;
   determine poses for at least the primary subject and the secondary subject within a plurality of frames from the given sequence of frames of image data;
   extract a set of parameters describing the poses and movement of at least the primary and secondary subjects from the plurality of frames from the given sequence of frames of image data;

detect a social behavior performed by at least the primary subject and involving at least the secondary subject, wherein the primary subject occludes at least a portion of the secondary subject, using a classifier trained to discriminate between a plurality of social behaviors based upon the set of parameters describing poses and movement of a plurality of subjects extracted from a plurality of frames of image data comprising depth information; and store the detected social behavior and an association with the primary subject in the at least one memory.

32. The behavioral classification system of claim 31, wherein the behavioral classification computer system is further directed to detect occurrence of modified social behavior resulting from administration of a pharmaceutical to a set of a plurality of primary subjects identified in the plurality of sequences of frames of image data based upon the detected social behaviors associated with the set of a plurality of primary subjects stored in the at least one memory.

33. The behavioral classification system of claim 32, wherein the behavioral classification computer system is further directed to:

detect a behavioral phenotype associated with a genotype shared by a set of a plurality of primary subjects identified in the plurality of sequences of frames of image data based upon:

the detected social behaviors associated with the set of a plurality of primary subjects stored in the at least one memory; and data describing a genotype of each of the primary subjects identified in the plurality of sequences of frames of image data.

34. An behavior classification system, comprising:

a microprocessor; and memory containing a classification application;

wherein the classification application directs the microprocessor to:

identify at least a primary subject interacting with a secondary subject within a sequence of frames of image data comprising depth information, where the sequence of frames of image data are captured from a viewpoint of the secondary subject;

determine poses for at least the primary subject within a plurality of frames from the sequence of frames of image data;

extract a set of parameters describing the poses and movement of at least the primary subject from the plurality of frames from the sequence of frames of image data; and detect a social behavior performed by the primary subject and involving at least the secondary subject, wherein the primary subject occludes at least a portion of the secondary subject, using a classifier trained to discriminate between a plurality of social behaviors based upon the set of parameters describing poses and movement of a first subject with respect to at least a second subject extracted from a plurality of frames of image data comprising depth information.

35. The behavioral classification system of claim 34, wherein:

the classifier is trained to discriminate between a plurality of social behaviors including aggressive and non-aggressive behaviors; and the detected social behavior performed by the primary subject is an aggressive behavior.

36. The behavioral classification system of claim 35, further comprising:

an output device;

wherein the classification application further directs the microprocessor to generate an alert via the output device based upon detection of an aggressive behavior.

37. A behavioral classification system, comprising:

a microprocessor;

memory containing a classification application;

wherein the classification application directs the microprocessor to:

identify a primary subject and a secondary subject within a sequence of frames of image data comprising depth information;

determine poses of the primary subject and the secondary subject within a plurality of frames from the sequence of frames of image data;

extract a set of parameters describing the poses and movement of the primary subject and the secondary subject from the plurality of frames from the sequence of frames of image data;

detect a behavior performed by at least the primary subject and involving at least the secondary subject, wherein the primary subject occludes at least a portion of the secondary subject, using a classifier trained to discriminate between a plurality of behaviors based upon the set of parameters describing poses and movement of a subject extracted from a plurality of frames of image data comprising depth information; and infer a genotype for the primary subject based upon behavior including the detected behavior performed by the primary subject.

38. The behavioral classification system of claim 37, wherein:

the detected behavior is a social behavior; and the classifier is trained to discriminate between a plurality of social behaviors based upon the set of parameters describing poses and movement of a plurality of subjects extracted from a plurality of frames of image data comprising depth information.

39. The behavioral classification system of claim 1, wherein the classification application further directs the microprocessor to:

compute a set of features based on the set of parameters, the set of features including relative positions between at least the primary subject and the secondary subject measured using at least a distance between a first portion of the primary subject and a second portion of the secondary subject; and wherein the social behavior is detected using a classifier trained to discriminate between a plurality of social behaviors based upon the relative positions between at least the primary subject and the secondary subject.

40. The behavioral classification system of claim 31, wherein the at least one microprocessor of the behavioral classification computer system is further directed by the classification application to:

for each of the sequences of frames of image data:

compute a set of features based on the set of parameters, the set of features including relative positions between at least the primary subject and the secondary subject measured using at least a distance between a first portion of the primary subject and a second portion of the secondary subject; and wherein the social behavior is detected using a classifier trained to discriminate between a plurality of social behaviors based upon the relative positions between at least the primary subject and the secondary subject.

41. The behavior classification system of claim 34, wherein the classification application further directs the microprocessor to:

compute a set of features based on the set of parameters, the set of features including relative positions between at least the primary subject and the secondary subject measured using at least a distance between a first portion of the primary subject and a second portion of the secondary subject; and wherein the social behavior is detected using a classifier trained to discriminate between a plurality of social behaviors based upon the relative positions between at least the primary subject and the secondary subject.

42. The behavioral classification system of claim 37, wherein the classification application further directs the microprocessor to:

compute a set of features based on the set of parameters, the set of features including relative positions between at least the primary subject and the secondary subject measured using at least a distance between a first portion of the primary subject and a second portion of the secondary subject;

wherein the social behavior is detected using a classifier trained to discriminate between a plurality of social behaviors based upon the relative positions between at least the primary subject and the secondary subject.

\* \* \* \* \*